US010767237B2

(12) United States Patent
Jansen et al.

(10) Patent No.: US 10,767,237 B2
(45) Date of Patent: Sep. 8, 2020

(54) METHODS OF REFINING A LIGNOCELLULOSIC HYDROLYSATE

(71) Applicant: VIRDIA, INC., Raceland, LA (US)

(72) Inventors: Robert Jansen, Collinsville, IL (US); Brendon Christopher Stout, Burlingtom, NC (US); Douglas Albert Walton, Springboro, OH (US)

(73) Assignee: VIRDIA, INC., Raceland, LA (US)

( * ) Notice: Subject to any disclaimer, the term of this patent is extended or adjusted under 35 U.S.C. 154(b) by 0 days.

(21) Appl. No.: 16/311,364

(22) PCT Filed: Jul. 5, 2017

(86) PCT No.: PCT/US2017/040658
§ 371 (c)(1),
(2) Date: Dec. 19, 2018

(87) PCT Pub. No.: WO2018/009502
PCT Pub. Date: Jan. 11, 2018

(65) Prior Publication Data
US 2019/0323096 A1    Oct. 24, 2019

Related U.S. Application Data

(60) Provisional application No. 62/359,145, filed on Jul. 6, 2016.

(51) Int. Cl.
*C13K 1/04*    (2006.01)
*B01D 11/04*    (2006.01)
(Continued)

(52) U.S. Cl.
CPC ............. *C13K 1/04* (2013.01); *B01D 11/048* (2013.01); *B01D 11/0488* (2013.01);
(Continued)

(58) Field of Classification Search
CPC .......... C13K 1/04; C13K 13/002; C13K 1/02; C13K 1/002; C13K 1/007; B01D 11/048;
(Continued)

(56) References Cited

U.S. PATENT DOCUMENTS 4,102,705 A    7/1978  Pfeiffer et al.
4,221,658 A *  9/1980  Hardwick .......... B01D 11/0449
                                                210/634
(Continued)

FOREIGN PATENT DOCUMENTS

CN    1270538 A    10/2000
CN    101279722 A  10/2008
(Continued)

OTHER PUBLICATIONS

Nils-Olof Nilvebrant et al, "Detoxification of Lignocellulose Hydrolysates with Ion Exchange Resins", published in Applied Biochemistry and Biotechnology, vol. 91-93, 2001, pp. 35-49 (Year: 2001).*

(Continued)

*Primary Examiner* — Joseph W Drodge
(74) *Attorney, Agent, or Firm* — Wilson Sonsini Goodrich & Rosati

(57) ABSTRACT

The present disclosure relates to lignocellulosic biomass processing and refining to produce hemicellulose and cellulose sugars. Methods and systems for refining a lignocellulosic hydrolysate are provided herein.

25 Claims, 10 Drawing Sheets

(51) Int. Cl.
  *C13K 13/00* (2006.01)
  *B01D 17/02* (2006.01)
  *B01J 41/08* (2017.01)
  *B01J 49/00* (2017.01)
  *B01D 11/00* (2006.01)

(52) U.S. Cl.
  CPC .......... *B01D 17/0217* (2013.01); *B01J 41/08* (2013.01); *B01J 49/00* (2013.01); *C13K 13/002* (2013.01); *B01D 2011/002* (2013.01)

(58) Field of Classification Search
  CPC .......... B01D 11/0488; B01D 2011/002; B01D 11/0476; B01D 11/0492; B01D 17/0217; B01D 15/02; C12P 2203/00; Y02P 20/582; B01J 41/00; B01J 20/30; B01J 20/3071; B01J 20/34; B01J 20/345; B01J 20/3475; B01J 41/02; B01J 41/04; B01J 41/08; B01J 41/09; B01J 41/10; B01J 47/00; B01J 47/011; B01J 47/10; B01J 49/00; B01J 49/07; B01J 49/57; B01J 2219/0027; B01J 2219/00029; B01J 2219/00031; B01J 2219/00033; C07H 1/06; C08B 37/0057; C08B 37/003; C07G 1/00; C08H 8/00
  USPC ........ 210/634, 638, 639, 787, 806; 127/1, 2, 127/9, 36, 42, 43, 46.1, 46.2, 48, 53, 56
  See application file for complete search history.

(56) References Cited

U.S. PATENT DOCUMENTS

| | | | |
|---|---|---|---|
| 4,247,340 A * | 1/1981 | Cartier | C08F 2/18 127/48 |
| 4,332,623 A | 6/1982 | Ando et al. | |
| 4,379,751 A | 4/1983 | Yoritomi et al. | |
| 4,563,337 A * | 1/1986 | Kim | B01D 61/243 210/257.2 |
| 4,608,245 A | 8/1986 | Gaddy et al. | |
| 4,970,002 A | 11/1990 | Ando et al. | |
| 5,102,553 A | 4/1992 | Kearney et al. | |
| 5,876,505 A * | 3/1999 | Klyosov | C13K 1/02 127/37 |
| 6,087,532 A | 7/2000 | Baniel et al. | |
| 6,093,326 A | 7/2000 | Heikkila et al. | |
| 6,187,204 B1 | 2/2001 | Heikkila et al. | |
| 6,207,824 B1 | 3/2001 | Henkes et al. | |
| 6,379,554 B1 | 4/2002 | Kearney et al. | |
| 6,391,204 B1 | 5/2002 | Russo, Jr. | |
| 6,451,123 B1 | 9/2002 | Saska et al. | |
| 7,465,791 B1 * | 12/2008 | Hallberg | B01D 3/002 530/500 |
| 8,641,910 B2 * | 2/2014 | Wietgrefe | C12P 7/10 210/634 |
| 8,728,320 B2 * | 5/2014 | Borden | B01J 20/24 127/1 |
| 9,068,206 B1 * | 6/2015 | Kwiatkowski | C12P 17/10 |
| 9,493,851 B2 * | 11/2016 | Jansen | C10L 1/02 |
| 2002/0153317 A1 | 10/2002 | Heikkila et al. | |
| 2003/0094416 A1 | 5/2003 | Heikkila et al. | |
| 2004/0231661 A1 * | 11/2004 | Griffin | C12P 7/10 127/1 |
| 2006/0191848 A1 * | 8/2006 | Ruffer | B01D 11/0488 210/631 |
| 2008/0041366 A1 | 2/2008 | Wahnon | |
| 2008/0057555 A1 * | 3/2008 | Nguyen | C12P 7/10 435/165 |
| 2008/0248540 A1 | 10/2008 | Yang | |
| 2008/0259034 A1 | 10/2008 | Lee et al. | |
| 2009/0056707 A1 * | 3/2009 | Foody | B01J 39/04 127/46.2 |
| 2009/0173339 A1 | 7/2009 | Heikkila et al. | |
| 2009/0176286 A1 * | 7/2009 | O'Connor | C08B 37/0003 435/139 |
| 2010/0013784 A1 | 1/2010 | Nashiki et al. | |
| 2010/0043784 A1 | 2/2010 | Jensen | |
| 2010/0124772 A1 | 5/2010 | Sabesan | |
| 2010/0189706 A1 * | 7/2010 | Chang | C12P 19/02 424/94.4 |
| 2011/0192560 A1 | 8/2011 | Heikkila et al. | |
| 2011/0318796 A1 * | 12/2011 | Walther | C12P 7/10 435/151 |
| 2012/0058526 A1 | 3/2012 | Jansen et al. | |
| 2013/0052709 A1 * | 2/2013 | Wietgrefe | C12P 7/10 435/162 |
| 2014/0054224 A1 * | 2/2014 | Erhardt | B01D 11/0492 210/638 |
| 2014/0162345 A1 * | 6/2014 | Eyal | C08H 8/00 435/253.6 |
| 2015/0087031 A1 | 3/2015 | Jansen et al. | |
| 2015/0128932 A1 * | 5/2015 | Kwiatkowski | C12P 17/10 127/9 |
| 2015/0136121 A1 * | 5/2015 | Jansen | C13K 11/00 127/55 |
| 2015/0183813 A1 * | 7/2015 | Eskelinen | C09J 197/005 530/507 |

FOREIGN PATENT DOCUMENTS

| | | |
|---|---|---|
| CN | 101548023 A | 9/2009 |
| CN | 101691587 A | 4/2010 |
| CN | 101977664 A | 2/2011 |
| EP | 0018621 A1 | 11/1980 |
| GB | 2240053 B | 8/1994 |
| JP | S4963659 A | 6/1974 |
| JP | S60146013 A | 8/1985 |
| JP | S61123601 A | 6/1986 |
| JP | 2002541355 A | 12/2002 |
| JP | 2010501013 A | 1/2010 |
| JP | 2011517445 A | 6/2011 |
| RU | 2105065 C1 | 2/1998 |
| WO | WO-8403304 A1 | 8/1984 |
| WO | WO-9426380 A1 | 11/1994 |
| WO | WO-9906133 A1 | 2/1999 |
| WO | WO-0061276 A1 | 10/2000 |
| WO | WO-03010339 A1 | 2/2003 |
| WO | WO-2008019468 A1 | 2/2008 |
| WO | WO-2008111045 A1 | 9/2008 |
| WO | WO-2009117317 A1 | 9/2009 |
| WO | WO-2009125400 A2 | 10/2009 |
| WO | WO-2009155982 A1 | 12/2009 |
| WO | WO-2010026572 A1 | 3/2010 |
| WO | WO-2010045576 A2 | 4/2010 |
| WO | WO-2010045576 A3 | 7/2010 |
| WO | WO-2011017797 A1 | 2/2011 |
| WO | WO-2011022812 A1 | 3/2011 |
| WO | WO-2011154604 A1 | 12/2011 |
| WO | WO-2011161685 A2 | 12/2011 |
| WO | WO-2012018740 A1 | 2/2012 |
| WO | WO-2012031270 A1 | 3/2012 |
| WO | WO-2013166469 A2 | 11/2013 |
| WO | WO-2015034964 A1 | 3/2015 |
| WO | WO-2016094878 A1 | 6/2016 |
| WO | WO-2016112134 A1 | 7/2016 |
| WO | WO-2016191503 A1 | 12/2016 |
| WO | WO-2018009502 A1 | 1/2018 |

OTHER PUBLICATIONS

Chan, et al. Methods for mitigation of bio-oil extract toxicity. Bioresour Technol. May 2010;101(10):3755-9. doi: 10.1016/j.biortech.2009.12.054. Epub Jan. 27, 2010.
Co-pending U.S. Appl. No. 62/359,145, filed Jul. 6, 2016.
Co-pending U.S. Appl. No. 61/680,183, filed Aug. 6, 2012.
EP17824776.3 Extended European Search Report dated Jan. 28, 2020.
Grzenia, et al. Detoxification of biomass hydrolysates by reactive membrane extraction. Journal of Membrane Science. vol. 348, Issues 1-2, Feb. 15, 2010, pp. 6-12.

(56) References Cited

OTHER PUBLICATIONS

Grzenia et al. Membrane extraction for detoxification of biomass hydrolysates. Bioresource Technology 111:248-254 (2012). Available online Feb. 8, 2012.

Grzenia, et al. Membrane extraction for removal of acetic acid from biomass hydrolysates. J Membr Sci 2008;322:189-195.

PCT/US2017/040658 International Search Report and Written Opinion dated Oct. 2, 2017.

Rasrendra, et al. Recovery of acetic acid from an aqueous pyrolysis oil phase by reactive extraction using tri-n-octylamine. Chemical Engineering Journal. Dec. 1, 2011; 176-177:244-252.

Wang et al. Cellulose extraction from wood chip in an ionic liquid 1-allyl-3-methylimidazolium chloride (AmimCl). Bioresour Technol. Sep. 2011;102(17):7959-65. doi: 10.1016/j.biortech.2011.05.064. Epub May 30, 2011.

\* cited by examiner

METHODS OF REFINING A LIGNOCELLULOSIC HYDROLYSATE

CROSS-REFERENCE

This application is a National Stage Entry of PCT/US2017/040658, filed on Jul. 5, 2017, which claims the benefit of U.S. Provisional Application No. 62/359,145, filed Jul. 6, 2016, each incorporated herein by reference in its entirety.

BACKGROUND OF THE INVENTION

Lignocellulosic biomass materials are renewable sources for production of amino acids for feed and food supplements, monomers and polymers for the plastic industry, and renewable sources for different types of fuels, polyol sugar substitutes (xylitol, sorbitol, manitols and the likes), and numerous other chemicals that can be synthesized from C5 and C6 sugars. Nonetheless, efficient and cost effective processes to extract C5 and C6 sugars from the biomass are still a challenge.

Classical sugar refining from corn milling comprises a sequence of resin-based ion exchangers to remove cations, anions, non-ionic compounds and color bodies. This technology has been well developed for starch hydrolysates since the 1960's and 70's and is still the method of production of sugars from corn and other easy to hydrolyze feedstocks.

It is well known that methods applied for producing $1^{st}$ generation sugars, i.e., from starch or sucrose feedstocks, are too costly when applied to $2^{nd}$ generation sugar production, i.e., from biomass. Biomass hydrolysis requires more severe conditions to effectively hydrolyze it as compared to starch. For example, stronger and/or more concentrated acids are used, and temperature and/or pressure of reactions are increased, all resulting in greater formation of degradation products that must be removed. Much of the increased cost is due in part to the impact of organic acids, which are an inherent component in biomass hydrolysates on the WBA resin.

The anions of biomass associated organic acids can be adsorbed by the WBA, but their adsorption is accompanied by a striking swelling of the resin, ten-fold greater than the swelling caused by mineral acid. Inherently, the resin holds a finite number of adsorption sites (e.g., the number of ammonium groups in a given volume of resin is finite), and once exhausted the resin is regenerated by: (i) washing the resin with water to recover sugar from the resin volume, yielding a "sweet water" having 2-4% sugars; (ii) periodic regeneration with mineral acid to remove the organic acid; (iii) regeneration with caustic or soda ash to prepare the resin for the next cycle; and (iv) a final wash to remove excess base. Consequently, when regenerating the resin with base, the resin shrinks. In the next adsorption cycle the resin swells again. The result of these swelling and shrinking cycles mechanically grinds the resin to dust, leading to poor mass transfer in washing, production and regeneration functions and eventually frequent need to replace the resin at high cost. When applied to refining of bagasse hemicellulose hydrolysate, the lifetime of a WBA resin is about half of that for the typical operation of refining corn sugars. Other feedstocks that release higher amounts of acetic acid in hydrolysis, such as eucalyptus, shorten the lifetime of the resin even more.

SUMMARY OF THE INVENTION

In view of the foregoing, there is a pressing need for efficient methods for refining and de-acidifying lignocellulosic hydrolysates at industrial scales. The present disclosure addresses this need by providing new methods and systems for refining hydrolysates with a liquid anion exchange medium. For industrial purposes, the methods described herein can be performed using industrially available means and machines that can support high production rates at low costs, while maintaining high purification power. It is the objective of the current disclosure to achieve such scaling up of the process to a size that allows producing at least 7,000 tons of purified xylose per annum, or more.

In certain aspects, the present disclosure provides a method for refining a lignocellulosic hydrolysate, comprising (a) contacting at least 250 parts of the lignocellulosic hydrolysate with 1 part of a liquid anion exchange medium (LAEM); and (b) recovering at least 225 parts of an aqueous stream, wherein the aqueous stream comprises one or more sugars. In some examples, the at least 250 parts comprise at least 1000 parts, and the at least 225 parts comprise at least 900 parts. The at least 250 parts may comprise at least 10,000 parts, and the at least 225 parts may comprise at least 9,000 parts. In some examples, the LAEM is recycled periodically. The contacting may occur in a continuous process. The continuous process may comprise steps of washing, neutralizing, and refining of the LAEM portion. In some examples, at any given time, a ratio of the LAEM to the lignocellulosic hydrolysate is less than 5:1. In some examples, the contacting occurs in a liquid-liquid separation centrifuge.

In certain aspects, the present disclosure provides a method for refining a lignocellulosic hydrolysate, comprising (a) contacting the lignocellulosic hydrolysate with a first portion of a liquid anion exchange medium (LAEM) in a liquid-liquid separation centrifuge to form a mixture; (b) separating the mixture in the liquid-liquid separation centrifuge into an organic stream and an aqueous stream, wherein the organic stream comprises the LAEM, an acid and an impurity, and wherein the aqueous stream comprises one or more sugars; (c) contacting the organic stream with a base, thereby forming a neutralized mixture; and (d) recovering a second portion of an LAEM from the neutralized mixture; wherein steps (a) through (b) are a continuous process. In some examples, steps (a) through (d) are a continuous process. In some examples, steps (a) through (d) are completed within 90 min. In some examples, steps (a) and (b) are completed within 60 min. Optionally, steps (a) and (b) are completed within 30 min. Optionally, steps (a) and (b) are completed within 15 min. Optionally, steps (a) and (b) are completed within 5 min. In some examples, the method further comprises washing the organic stream with water to remove residual sugar from the organic stream, thereby forming a dilute sugar water solution and a washed organic stream. In some examples, the dilute sugar water solution is combined with the aqueous stream, wherein the combined stream comprises at least 3.8% wt/wt sugars. In some examples, the base is added as an aqueous suspension or solution. The base may be lime. In some examples, the base is added as an aqueous solution. The base may be NaOH. In some examples, the pH of the neutralized mixture is between 6 and 7. In some examples, the method comprises washing the second portion of an LAEM with water, thereby forming a washed LAEM. A portion of the washed LAEM may be contacted with a second base. The portion of the washed LAEM may comprise less than 20% of the washed LAEM. Optionally, the pH of the base is at least 13.

In some examples, the method further comprises repeating steps (a)-(d), wherein the second portion of a LAEM recovered in step (d) is reused in step (a) as the first portion of a LAEM when repeating the steps (a)-(d). The volume of the second portion of an LAEM after the repeating may be at least 80% of the volume of the first portion of an LAEM before the repeating. The volume of the second portion of an LAEM after the repeating may be at least 90% of the volume of the first portion of an LAEM before the repeating. The volume of the second portion of an LAEM after the repeating may be at least 95% of the volume of the first portion of an LAEM before the repeating, such as at least 97.5% of the volume of the first portion of an LAEM before the repeating. In some examples, the method is repeated at least 45 times in a day. In some examples, the ratio of the first portion of an LAEM to the lignocellulo sic hydrolysate is less than 5:1. In some examples, the LAEM comprises an amine, wherein the amine comprises at least 20 carbon atoms. The amine may be a tertiary amine, such as tri-laurylamine. In some examples, the LAEM further comprises a diluent. The diluent may comprise a $C_{6-16}$ alcohol or kerosene, such as hexanol or 2-ethylhexanol. The diluent may be 2-ethylhexanol. In some examples, the ratio of the amine to the diluent is between 1:7 and 7:1 weight/weight. In some examples, the lignocellulosic hydrolysate comprises at least 0.1% acid weight/weight. The lignocellulosic hydrolysate may comprise at least 0.5% acid weight/weight.

In some examples, the acid comprises an inorganic acid and an organic acid. In some examples, the aqueous stream comprises less than 200 ppm calcium. In some examples, the aqueous stream comprises arabinose in an amount up to 12% weight/weight relative to total dissolved sugars. In some examples, the aqueous stream comprises disaccharides in an amount up to 8% weight/weight relative to total dissolved sugars. In some examples, the aqueous stream comprises ash in an amount up to 0.25% weight/weight. In some examples, the aqueous stream comprises less than 1000 ppm acetic acid. In some examples, the aqueous stream comprises less than 1000 ppm formic acid. In some examples, the aqueous stream comprises less than 1000 ppm sulfuric acid. In some examples, the aqueous stream comprises less than 1000 ppm hydrochloric acid. In some examples, the aqueous stream comprises less than 0.5% weight/weight acid, such as less than 0.1% weight/weight acid. In some examples, the aqueous stream comprises phenolic compounds in an amount up to 500 ppm. In some examples, the aqueous stream comprises furfural in an amount up to 500 ppm. In some examples, the aqueous stream comprises nitrogen in an amount up to 1000 ppm.

In certain aspects, the present disclosure provides a system for refining a lignocellulo sic hydrolysate, comprising (a) a hydrolysate refining unit comprising a first inlet to receive a lignocellulosic hydrolysate stream, a second inlet to receive a recycled LAEM stream, a first outlet to release an organic stream, and a second outlet to release an aqueous stream; and (b) a neutralization unit in fluid communication with the hydrolysate refining unit, wherein the neutralization unit comprises an inlet to receive the organic stream and a second inlet to receive a base, wherein the neutralization unit is configured to convert the organic stream to the recycled LAEM stream, and further wherein the neutralization unit comprises a first outlet to release the recycled LAEM stream in fluid communication with the second inlet of the hydrolysate refining unit. In some examples, the hydrolysate refining unit comprises a mixer-settler device, a centrifuge, a stirred tank, a column, or a combination thereof. The hydrolysate refining unit may comprise a centrifuge. The centrifuge may be a liquid-liquid separation centrifuge. The hydrolysate refining unit may comprise at least two liquid-liquid separation centrifuges.

In some examples, the hydrolysate refining unit is in fluid communication with an LAEM refining unit, wherein the LAEM refining unit comprises an inlet to receive the organic stream. The LAEM refining unit may comprise an outlet to release an entrained sugar stream and a loaded organic stream. The LAEM refining unit may comprise a centrifuge or a static mixer and a decanter centrifuge. In some examples, the neutralization unit comprises a liquid-liquid separation centrifuge. The neutralization unit may comprise a mixing tank configured to mix the organic stream and the base. The neutralization unit may be in fluid communication with a cleaning unit. In some examples, the cleaning unit comprises an inlet to receive at least 5% of the recycled LAEM stream, and wherein the cleaning unit is configured to contact the recycled LAEM stream with a base, thereby forming a mixture. The cleaning unit may comprise an outlet to release the mixture into the neutralization unit.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. Application Nos. 62/359,145 and 61/680,183 and PCT Application Nos. PCT/US2013/039585, PCT/US2014/053956, and PCT/US2016/012384 are herein incorporated by reference in their entireties.

DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
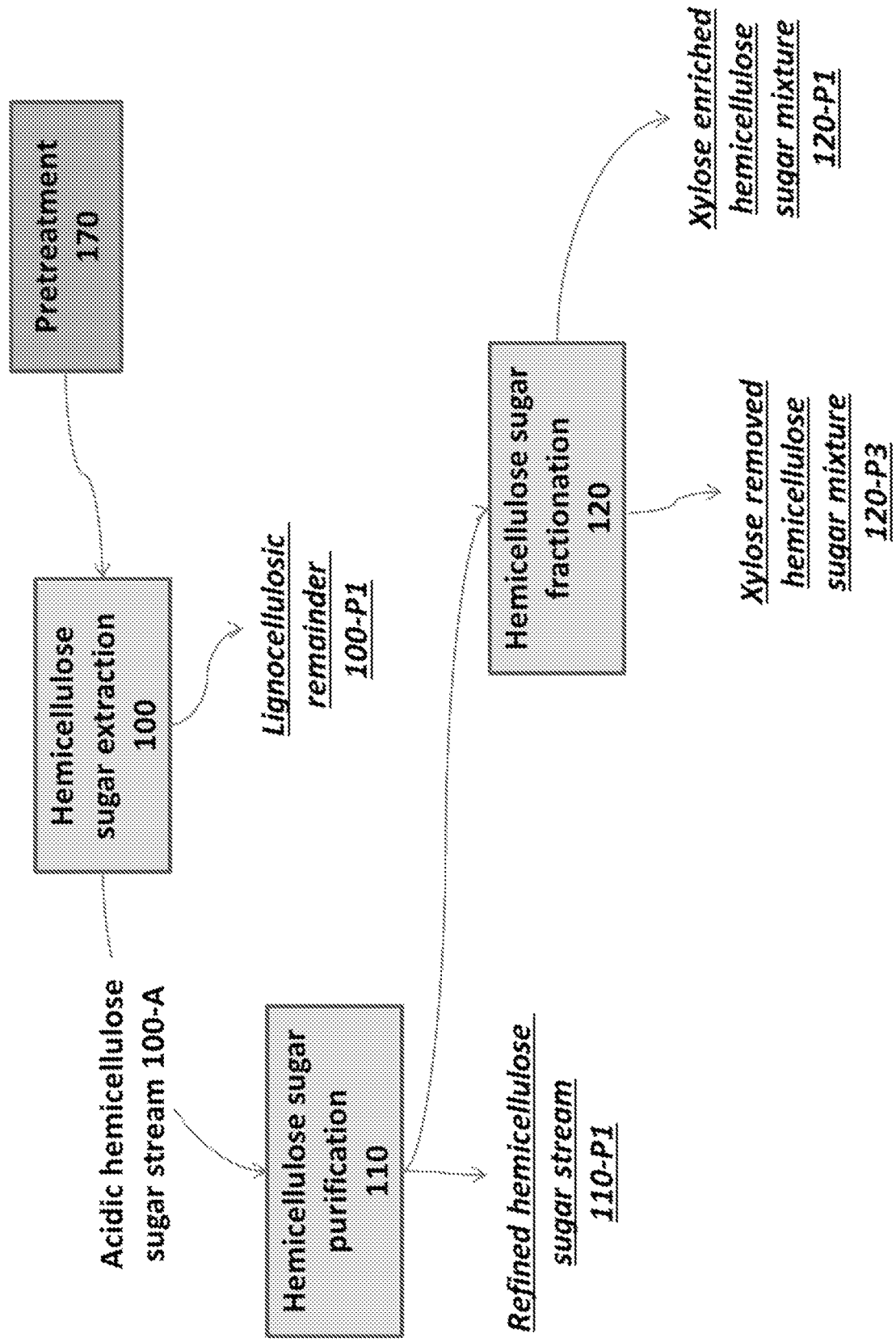
FIG. 1 shows a schematic overview of the exemplary conversion processes to convert biomass to a refined hemicellulose sugar stream.

While various embodiments of the invention(s) of the present disclosure have been shown and described herein, it will be obvious to those skilled in the art that such embodiments are provided by way of example only. Numerous variations, changes, and substitutions may occur to those skilled in the art without departing from the invention(s). It should be understood that various alternatives to the embodiments of the invention(s) described herein may be employed in practicing any one of the invention(s) set forth herein.

The present disclosure relates to lignocellulosic biomass processing and refining to produce hemicellulose and cellulose sugars, and the conversion thereof to high-value products. In particular, the present disclosure provides methods and systems for refining a lignocellulosic hydrolysate. The methods and systems described herein are particularly effective at removing acids and impurities from a lignocellulosic hydrolysate on an industrial scale at high efficiency. Methods and systems for recycling various streams in the process are also described.

The terms "liquid anion exchange medium" and "LAEM", as used herein, generally refer to a weak base anion exchanger in the liquid form. Typically, the LAEM may have very low water solubility (e.g. 10 g/100 g of water at 25° C.). The LAEM may comprise an amine that can extract non-ionic impurities. During the extraction, the amine may have similar functional groups as a WBA resin. The LAEM may further be dissolved in a solvent (e.g., diluent). Preferably, the diluent may (i) dissolve well both the free tertiary amine $R_3N$ and its bound form $R_3NH^+A^-$; (ii) control viscosity at an industrially useful range, allowing utilization of low cost systems such as mixer-settlers and/or liquid-liquid centrifuges; (iii) contribute further to the capacity of the solvent to extract non-ionic impurities; and/or (iv) allow regeneration of the loaded phase by efficient contact with mineral bases such as caustic or lime.

In certain aspects, the present disclosure provides a method for refining a lignocellulosic hydrolysate. In some examples, the method comprises (a) contacting at least 250 parts of the lignocellulosic hydrolysate with 1 part of a liquid anion exchange medium (LAEM) and (b) recovering at least 225 parts of an aqueous stream, wherein the aqueous stream comprises one or more sugars.

In certain aspects, the present disclosure provides a method for refining a lignocellulosic hydrolysate. In some examples, the method comprises (a) contacting the lignocellulosic hydrolysate with a first portion of a liquid anion exchange medium (LAEM) in a liquid-liquid separation centrifuge to form a mixture, (b) separating the mixture in the liquid-liquid separation centrifuge into an organic stream and an aqueous stream, wherein the organic stream comprises the LAEM, an acid and an impurity, and wherein the aqueous stream comprises one or more sugars, (c) contacting the organic stream with a base, thereby forming a neutralized mixture, and (d) recovering a second portion of an LAEM from the neutralized mixture. Steps (a) and (b) may be continuous. Optionally, steps (a) through (d) are continuous. The aqueous stream is also referred to herein as a "refined hemicellulose sugar stream".

The lignocellulosic hydrolysate may result from hydrolysis of a lignocellulosic biomass. A biomass embodied in a subject method or system disclosed herein is typically high in xylan content. The biomass may be derived from wood, softwood, hardwood such as alder, aspen, birch, beech, maple, poplar, eucalyptus, and willow, plants or plant constituents, grains such as wheat, barley, rice, rye and oat, particulates of grain such as straw, hulls, husks, fiber, shells, and stems, corn cobs, corn straw, corn fiber, nutshells, almond shells, coconut shells, bagasse, cottonseed bran, and cottonseed skins. When wood is used as a starting material, it is advantageously used as chips or sawdust. Preferably, the biomass is selected from hardwood, such as birch and eucalyptus, bagasse, and sugarcane leaves, or a combination thereof. Optionally, the biomass comprises one or more of sugarcane bagasse and sugarcane leaves.

A lignocellulosic hydrolysate may be produced from feeds selected from new bagasse, piled bagasse (more than 4 years) and sugar cane leaves. Hemicellulose sugars may be extracted from sugar cane leaves and other grasses to produce the hydrolysate. Optionally, biomass feedstocks are mixed prior to hydrolysis. For example, a mixture of sugar cane bagasse and sugar cane leaves may be hydrolyzed together. Optionally, different hydrolysate streams are mixed. For example, a hydrolysate of sugar cane bagasse and a hydrolysate of sugar cane leaves may be mixed prior to refining (e.g., LAEM refining). Optionally, streams derived from different feedstocks are mixed after refining (e.g., LAEM refining). Two types of feed may be available for making xylose. A method described herein may use two feed streams that are combined together at the LAEM refining process. For example bagasse, old or new, may undergo the sequence of de-ashing, hemicellulose extraction, and LAEM refining. In another example, the leaves may undergo the sequence of hemicellulose extraction to LAEM refining.

Leaves may be collected and baled at the field and brought into the plant. The leaves may not contain the high amounts of "physical" ash, for example, sand grains, as the bagasse does, in which case, there may not be a need for de-ashing. Advantages of using leaves are described in PCT/US2016/012384. Extraction conditions can be optimized separately for each feed. The conditions may be milder for leaves. Both feeds can be combined together from the refining step onwards, despite the difference in sugar composition in their respective hydrolysates and the different levels of various contaminants. The process can maintain both types of hydrolysates at high xylose levels of at least about 50%, at least about 55%, at least about 60%, at least about 65%, at least about 70%, or at least about 75% wt/wt of xylose/total monomers.

Figure 2:
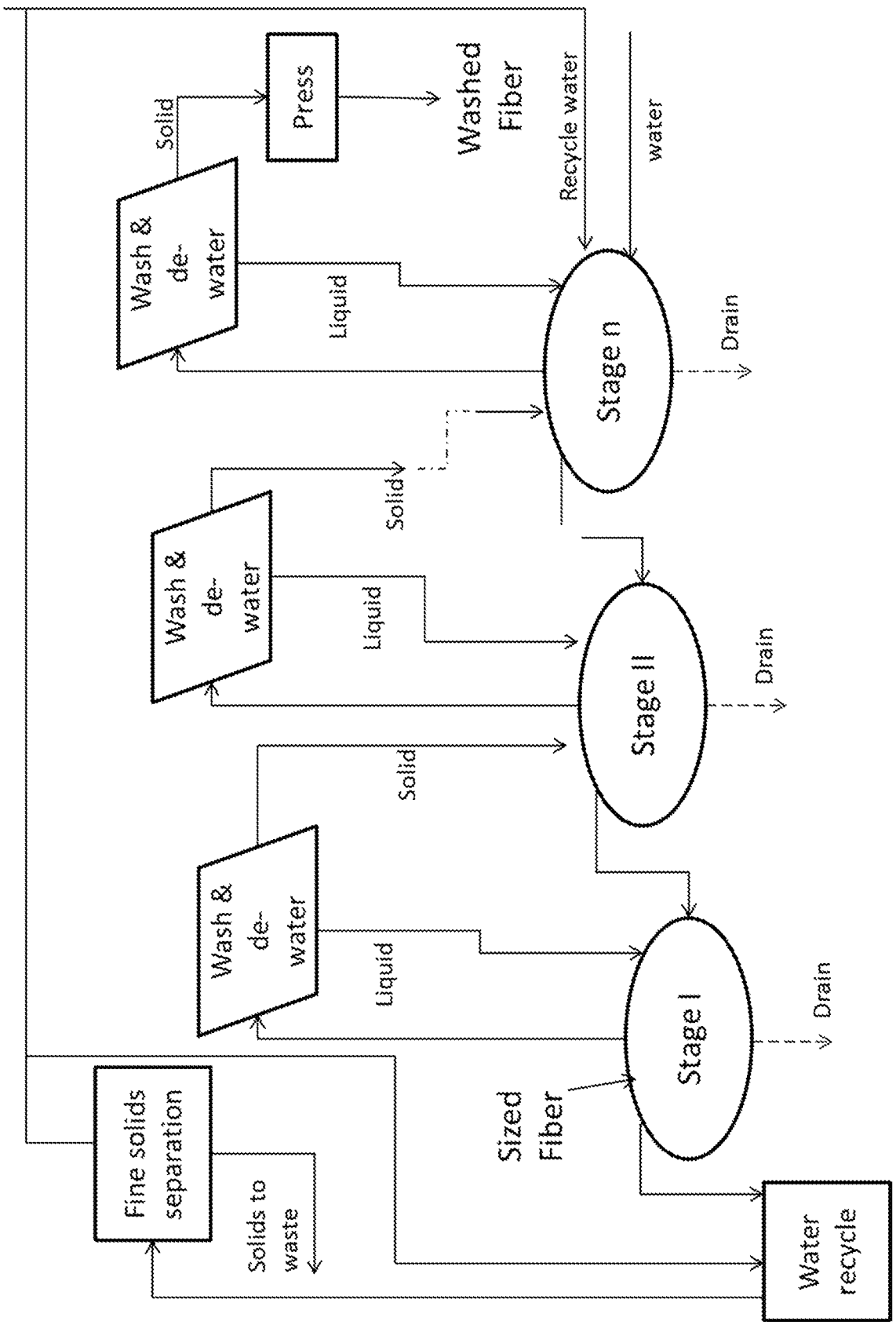
FIG. 2 illustrates a schematic diagram of exemplary sequential processes for washing biomass.

A schematic of exemplary conversion processes to convert biomass to a refined hemicellulose sugar stream is provided in FIG. 1. Optionally, lignocellulose-containing biomass is pre-treated (170) prior to extracting hemicellulose sugars. In some examples, pretreatment of the biomass may not be required, i.e., the lignocellulose-containing biomass can be used directly in the hemicellulose sugar extraction. A schematic diagram of exemplary counter current processes for washing biomass is provided in FIG. 2. Pretreatment may comprise a reduction in biomass size (e.g., mechanical breakdown, milling, or grinding). Optionally, the lignocellulose-containing biomass is ground such that the average size of the resultant biomass particles is between about 100 to 1,000 microns, such as about 400-5,000 microns, about 100-400 microns, about 400-1,000 microns, about 1,000-3,000 microns, about 3,000-5,000 microns, or about 5,000-10,000 microns. The average size of the ground biomass particles may be less than 10,000 microns, less than 9,000 microns, less than 8,000 microns, less than 7,000 microns, less than 6,000 microns, less than 5,000 microns, less than 4,000 microns, less than 3,000 microns, less than 2,000 microns, less than 1,000 microns, or less than 500 microns.

Pretreatment of the lignocellulose-containing biomass may comprise reducing ash and soil content of the biomass prior to extracting hemicellulose sugars from the biomass. In some examples, lignocellulose-containing biomass comprising greater than about 4% wt/wt, greater than about 5% wt/wt, greater than about 6% wt/wt, greater than about 7% wt/wt, or greater than about 8% wt/wt of apparent ash, such as 4% to 8% wt/wt of apparent ash (as measured by ashing a dry sample of the biomass according to NREL/TP-510-42622) is de-soiled and de-ashed. Ash values greater than about 4% may be indicative of physical incorporation of soil particles in the biomass during the growing season, wherein the soil particles contact and are encased by the biomass as it grows. Reducing ash and soil content of the biomass may comprise one or more stages of slurrying, washing, and dewatering the biomass. A method for reducing ash and soil content may comprise at least one and up to n stages of re-slurry and milling (e.g., grinding) the biomass, and at least one and up to m stages of washing and dewatering the biomass, wherein n is 2, 3, 4, 5, 6, 7, 8, 9 or 10 and m is 2, 3, 4, 5, 6, 7, 8, 9 or 10. Optionally, n is equal to m. In some examples, m is greater than n or n is greater than m. Two or more such cycles of shear treatment and high pressure washing may be necessary to reduce the ash content of the biomass to less than 6%, less than 5%, less than 4%, or less than 3% wt/wt of ash, such as 3%-6% wt/wt of ash.

Hemicellulose sugars may be extracted from lignocellulosic biomass by any suitable method (100, FIG. 1), for example, using an aqueous acidic solution. The aqueous acidic solution may comprise any acid, such as an inorganic acid or an organic acid. Preferably, the solution can comprise an inorganic acid, such as $H_2SO_4$, $H_2SO_3$ (which can be introduced as dissolved acid or as $SO_2$ gas), or HCl. In some examples, the aqueous acidic solution may comprise an inorganic and/or an organic acid, including, for example, $H_2SO_4$, $H_2SO_3$, HCl, or acetic acid, or combinations thereof. In some examples, the aqueous acidic solution does not comprise HCl. The acidic aqueous solution can contain an acid in an amount of about 0 to 2% acid or more, such as about 0-1.0%, about 0-1.5%, about 0.5-1.5%, about 0.5-2.0%, about 1.0-2.0%, about 1.5-2.0%, about 0.2-1.0%, about 0.2-0.7%, about 0-0.2%, about 0.2-0.4%, about 0.4-0.6%, about 0.6-0.8%, about 0.8-1.0%, about 1.0-1.2%, about 1.2-1.4%, about 1.4-1.6%, about 1.6-1.8%, or about 1.8-2.0% wt/wt. Optionally, the aqueous solution for the extraction includes 0.2-0.7% $H_2SO_4$ and 0-3,000 ppm $SO_2$. The pH of the acidic aqueous solution may be in the range of about pH 1 to pH 5, such as about pH 1 to pH 3.5.

Elevated temperature or pressure may be used to extract hemicellulose sugars from biomass. In some examples, a temperature in the range of about 100-200° C. can be used. A temperature of greater than 50° C., greater than 60° C., greater than 70° C., greater than 80° C., greater than 90° C., greater than 100° C., greater than 110° C., greater than 120° C., greater than 130° C., greater than 140° C., greater than 150° C., greater than 160° C., greater than 170° C., greater than 180° C., greater than 190° C., or greater than 200° C., such as 60° C. to 190° C. can be used in the extraction. Preferably, the temperature is in the range of 90–170° C., such as 100-165° C., 110-160° C., 120-150° C., 130-155° C. or 140-150° C. The pressure can be in the range of about 0.4-10 mPa, such as 0.4-5 mPa. Optionally, the pressure is less than 20 mPa, such as less than 10 mPa, less than 9 mPa, less than 8 mPa, less than 7 mPa, less than 6 mPa, or less than 5 mPa. In some examples, the extraction mixture can be heated for 0.1-5 hours, preferably 0.1-3 hours, 0.1-1 hour, 0.5-1.5 hours, 0.5-2 hours, 1-2 hours, or 2-3 hours. The extraction process can have a cooling down period of less than one hour. Optionally, hemicellulose sugars are extracted from biomass by contacting the biomass with an aqueous acidic solution and heating the resultant mixture to a temperature of greater than 50° C. at a pressure of less than 10 mPa.

Hemicellulose sugar extraction can produce, in one single extraction process, a hemicellulose sugar stream (100-A) containing at least 75% monomeric sugars, such as more than 80%, more than 85%, more than 90%, more than 91%, more than 92%, more than 93%, more than 94%, more than 95%, more than 96%, more than 97%, more than 98%, or more than 99% monomeric sugars. The hemicellulose sugar stream may contain 80-99% monomeric sugars. In some examples, at least about 70%, at least 75%, at least 80%, at least 85%, at least 90%, or even at least 95% or more of the hemicellulose sugars, such as 70% to 95% of the hemicellulose sugars present in the biomass can be extracted using a method of the disclosure. Hemicellulose sugar extraction may produce minimal amounts of lignocellulose degradation products, such as furfural, hydroxymethyl furfural, levulinic acid, and formic acid. A xylose yield of greater than 70%, optionally greater than 80%, of theoretical value can be achieved.

Figure 3:
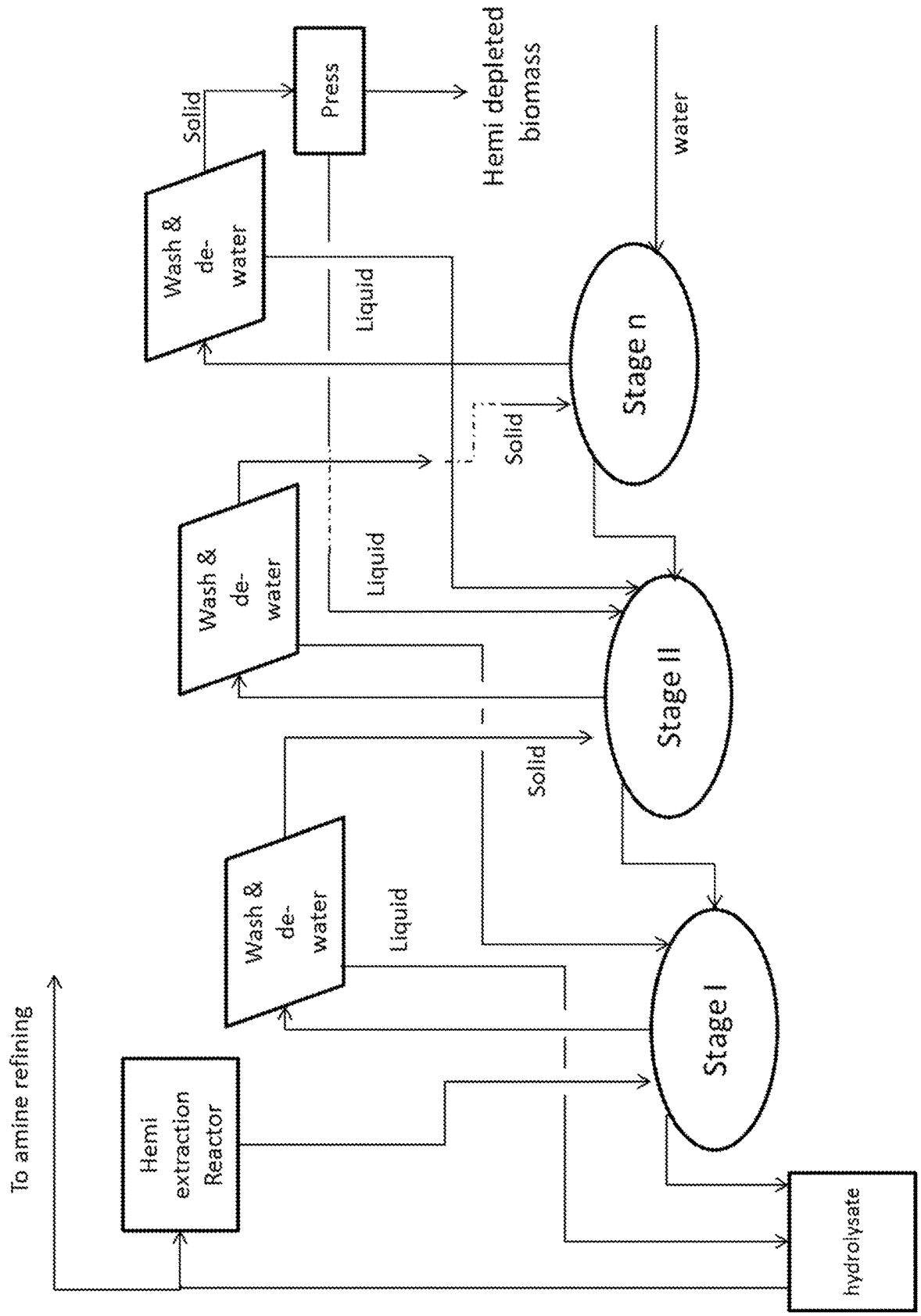
FIG. 3 illustrates a schematic diagram of exemplary sequential processes for washing and de-watering lignocellulosic biomass after extraction of hemicellulose sugars.

The extraction of hemicellulose sugars from the biomass can result in a lignocellulose remainder stream (100-P1) comprising lignin and cellulose. A schematic diagram of exemplary sequential processes for washing and de-watering a lignocellulose remainder stream after extraction of hemicellulose sugars is provided in FIG. 3. Alternatively, the lignocellulose remainder stream may be separated from the hemicellulose sugar stream by means of a vacuum belt filter and/or a filter press system. Vacuum belt filter systems are commercially available from various suppliers, including, for example, Pannevis, BHS-Sonthofen Inc. and FLSmidth. In some examples, the extraction slurry may be continuously fed over a moving belt. As the belt moves, vacuum may be applied to remove liquids and create a filtration cake resting on the moving belt. Optionally, the belt may pass through a wash zone. Optionally, the belt can pass through a drying zone. A wash zone may comprise nozzles that spray a wash fluid on the filtration cake (i.e., the lignocellulose remainder stream) to rinse residual hemicellulose sugars from the lignocellulose remainder stream, thereby increasing the recovery of hemicellulose sugars.

In some examples, the extraction of hemicellulose sugars may not remove a substantial amount of the cellulosic sugars. For example, extraction of hemicellulose sugars may not remove more than 1%, more than 2%, more than 5%, more than 10%, more than 15%, more than 20%, more than 30%, more than 40%, more than 50%, or more than 60% weight/weight of cellulose, such as 2%-40% weight/weight of cellulose. In some examples, the lignocellulose remainder stream comprises less than 50%, less than 45%, less than 40%, less than 35%, less than 30%, less than 25%, less than 20%, less than 15%, less than 10%, less than 5%, less than 2%, or less than 1% weight/weight of hemicellulose, such as 2% to 45% weight/weight of hemicellulose. The lignocellulose remainder stream may comprise less than 10%, less than 9%, less than 8%, less than 7%, less than 6%, less than 5%, less than 4%, less than 3%, less than 2%, or less than 1% weight/weight of ash, such as 2% to 9% weight/weight of ash. In some examples, the lignocellulose remainder stream comprises 0.001-5% weight/weight ash, such as 0.01-4%, 0.1-3%, 0.1-2%, or 0.1-1% weight/weight of ash. In some examples, the lignocellulose remainder stream comprises lignin, cellulose, hemicellulose in an amount less than 5% weight/weight, and ash in an amount less than 4% weight/weight. In some examples, less than 10%, less than 5%, less than 4%, less than 3%, less than 2.5%, less than 2%, less than 1.5%, or less than 1% of the lignocellulose solids, such as 1% to 5% of the lignocellulose solids remain in the hemicellulose sugar stream. Optionally, the lignocellulose remainder stream comprises less than 75%, less than 65%, less than 55%, less than 45%, less than 35%, less than 25%, less than 15%, or less than 10% weight/weight of water, such as 15% to 65% weight/weight of water. The lignocellulose remainder stream may comprise more than 20%, more than 30%, more than 40%, more than 50%, more than 60%, more than 70%, or more than 80% weight/weight of solids, such as 30% to 70% weight/weight of solids. The lignocellulose remainder stream may comprise less than 10%, less than 7.5%, less than 5%, less than 4%, less than 3%, less than 2%, less than 1%, or less than 0.5% weight/ weight of residual soluble carbohydrates. In some examples, the lignocellulose remainder stream comprises about 0.01- 5% weight/weight soluble carbohydrates, such as 0.1-5%, 0.5-5%, 0.5-2.5%, or 0.1-2.5% weight/weight of soluble carbohydrates. The lignocellulose remainder stream may comprise less than 5%, less than 4%, less than 3%, less than 2%, less than 1%, less than 0.5%, less than 0.2%, or less than 0.1% weight/weight of sulfate. In some examples, the lignocellulose remainder stream comprises 0.001-3% weight/ weight sulfate, such as 0.01-3%, 0.01-2%, 0.01-1%, or 0.001-1% weight/weight of sulfate. The lignocellulose remainder stream may comprise soluble carbohydrates in an amount relative to total solids of less than 5%, ash in an amount relative to total solids of less than 4%, and sulfate in an amount relative to total solids of less than 3%.

Impurities such as ash, acid soluble lignin, furfural, fatty acids, organic acids such as acetic acid and formic acid, methanol, proteins and/or amino acids, glycerol, sterols, rosin acid or waxy materials, or combinations thereof, can be extracted together with the hemicellulose sugars under the same conditions into the hemicellulose sugar stream. At least some of these impurities can be separated from the hemicellulose sugar stream by solvent extraction (e.g., using an LAEM).

The hemicellulose sugar stream can be refined and optionally fractionated according to processes disclosed in PCT/ US2013/039585, incorporated herein by reference. The hemicellulose sugar stream can be optionally filtered, centrifuged, or concentrated by evaporation. Optionally, the hemicellulose sugar stream is contacted with a strong acid cation exchanger (e.g., in H$^+$ form) to convert salts to the respective acids. In some examples, the hemicellulose sugar stream may be first contacted with a strong cation exchange resin and then contacted with an LAEM.

Prior to hemicellulose sugar purification 110, the acidic hemicellulose sugar stream 100-A from the hemicellulose sugar extraction 100 can be optionally filtered, centrifuged, or concentrated by evaporation. For example, the hemicellulose sugar stream can be contacted with strong acid cation exchanger (e.g., in H$^+$ form) to convert all salts to their respective acids.

Figure 4:
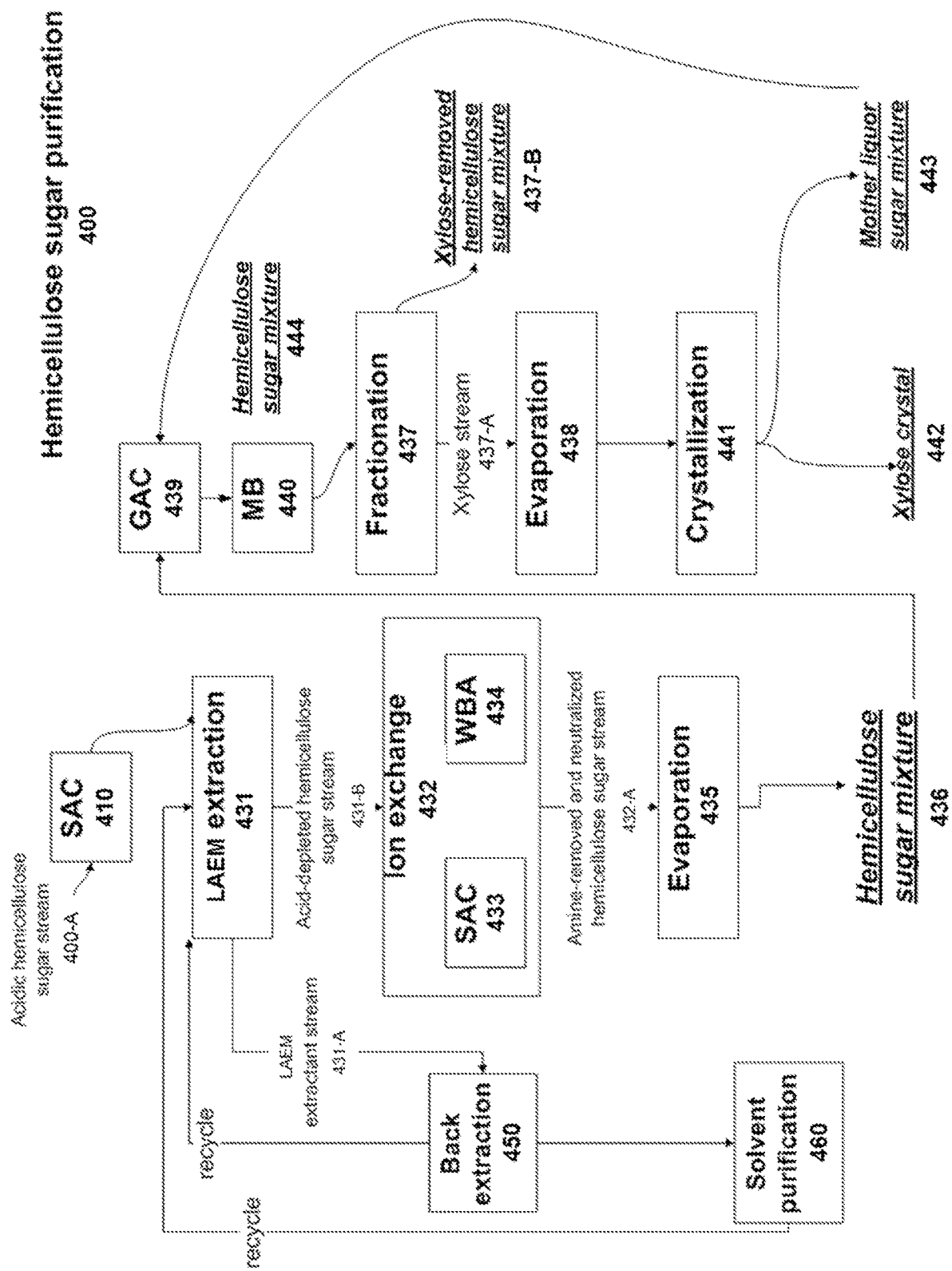
FIG. 4 is a schematic representation of an exemplary method of hemicellulose sugar extraction and purification according to some embodiments of the present disclosure. GAC stands for granulated activated carbon. MB stands for mixed bed (e.g., mixed bed cation/anion resin).

The hemicellulose sugar purification 400 is illustrated in greater details according to an exemplary embodiment of the present disclosure as shown in FIG. 4. As illustrated in FIG. 4, the acidic hemicellulose sugar stream 400-A is first subject to a strong cation exchange resin and then LAEM extraction 431, during which acids and impurities are extracted from the hemicellulose sugar stream into the LAEM. The acids-depleted hemicellulose sugar stream 431-B is then purified by ion exchange 432, including a strong acid cation exchanger (SAC) 433 and optionally followed by a weak base anion exchanger (WBA) 434. The amine-removed and neutralized hemicellulose sugar stream 432-A is optionally evaporated 435 to form a hemicellulose sugar mixture 436. Optionally, the amine removed and neutralized hemicellulose sugar stream 432-A may also be refined by contact with granulated activated carbon prior to evaporation 435.

Figure 6:
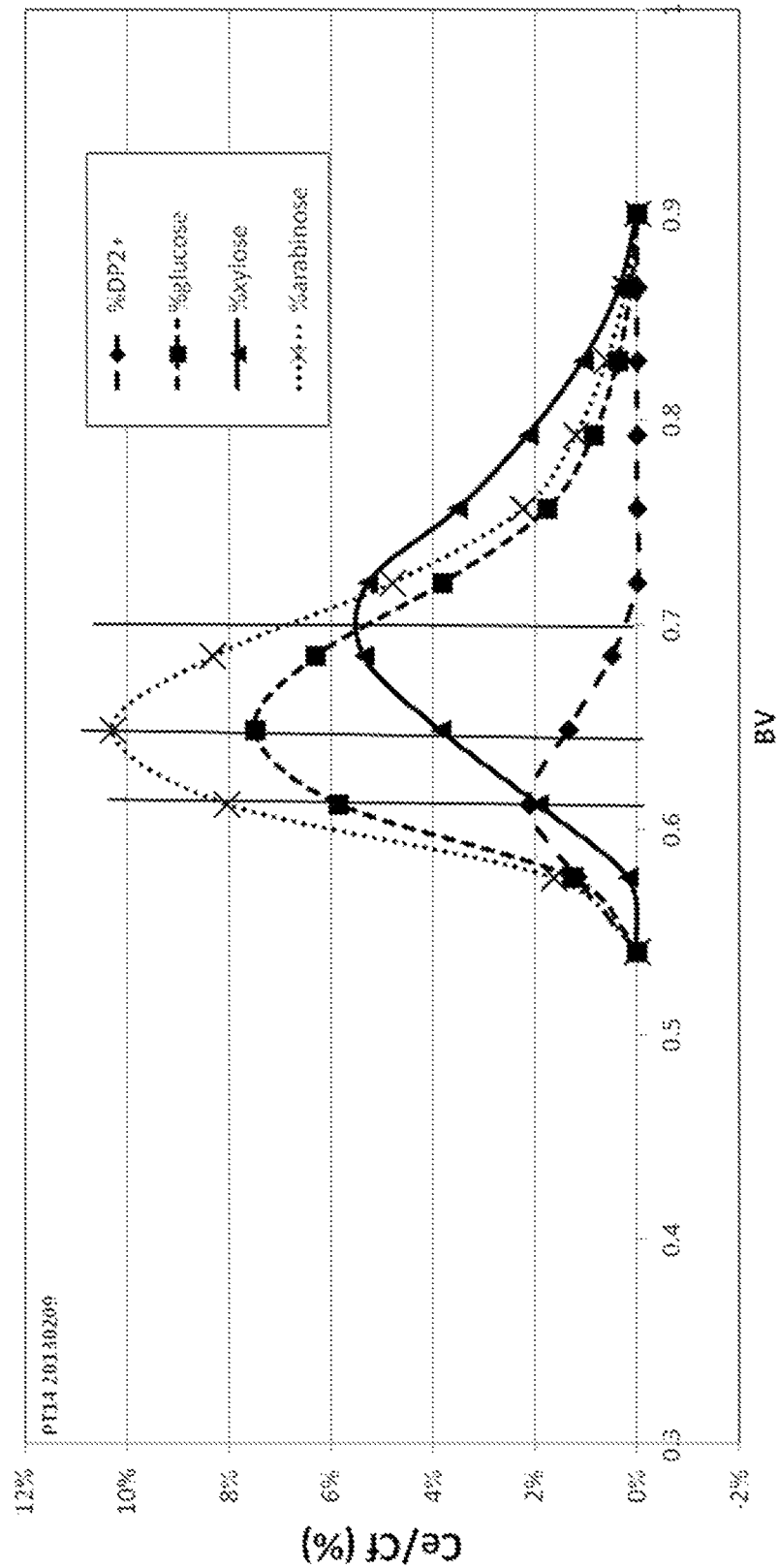
FIG. 6 depicts a chromatographic fractionation of a refined sugar mix to obtain an enriched xylose fraction and a mix sugar solution containing glucose, arabinose and a variety of DP2+ components.

The hemicellulose sugar mixture 436 can be refined by contacting with granulated activated carbon 439 and refined with mixed bed 440 prior to evaporation to higher concentration (process 1838 in FIG. 4) to yield a hemicellulose sugar mixture 444. The hemicellulose sugar mixture 436 can be optionally fractionated (process 437 in FIG. 4) to obtain high purity C5 sugars such as xylose. Fractionation can be carried out by any means, preferably using a simulated moving bed (SMB) or sequential simulated moving bed (SSMB). The fractionation may yield a xylose-removed hemicellulose sugar mixture (120-P3 and 437-B). Examples of simulated moving bed processes are disclosed, for instance, in U.S. Pat. Nos. 6,379,554, 5,102,553, 6,093,326, and 6,187,204, examples of sequential simulated moving bed processes can be found in GB 2 240 053 and U.S. Pat. No. 4,332,623 as well as U.S. Pat. Nos. 4,379,751 and 4,970,002, each of the contents of the entirety of which is incorporated herein by this reference. In an exemplary SMB or SSMB setup, the resin bed is divided into a series of discrete vessels, each of which can be sequenced through a series of 4 zones (feed, separation, feed/separation/raffinate and safety) and connected by a recirculation loop. A manifold system can connect the vessels and can direct, in appropriate sequence to (or from) each vessel, each of the four media accommodated by the process. Those media may be generally referred to as feed, eluent, extract and raffinate. For example, a feed can be hemicellulose sugar mixture 436, the eluent can be water, the extract is an enriched solution of xylose and the raffinate is an aqueous solution containing high molecular weight sugars and other monomeric sugars i.e. arabinose, galactose and glucose. Optionally, the eluent can be an aqueous solution comprising low concentration of hydroxide ion to maintain the resin in hydroxyl form, or the eluent can be an aqueous solution comprising a low concentration of acid to maintain the resin in a protonated form. For example, a feed comprising 30% sugar mix where xylose is about 65-70% of the mix can be fractionated using a SSMB to obtain an extract comprising about 16-20% sugars where xylose is about 82% or more and a raffinate comprising 5-7% sugar mix with only 15-18% xylose. FIG. 6 depicts a chromatographic fractionation of a refined sugar mix to obtain an enriched xylose fraction and a mix sugar solution containing glucose, arabinose and a variety of DP2+ components.

When an SSMB process is used for fractionation, xylose can exit from the extract flow and the higher sugars as well as glucose, galactose and arabinose can exit from the raffinate flow. The xylose stream (120-P3 and 437-A) can optionally be refined by contacting with granulated activated carbon and refined with mixed bed prior to evaporation to higher concentration (process 438 in FIG. 4). The refined xylose stream 437-A is then optionally evaporated again and crystallized (see, e.g., processes denoted in FIG. 4 by the number 441). The products can be a xylose crystal 442 and xylose-removed hemicellulose sugar mixture 443.

Figure 5:
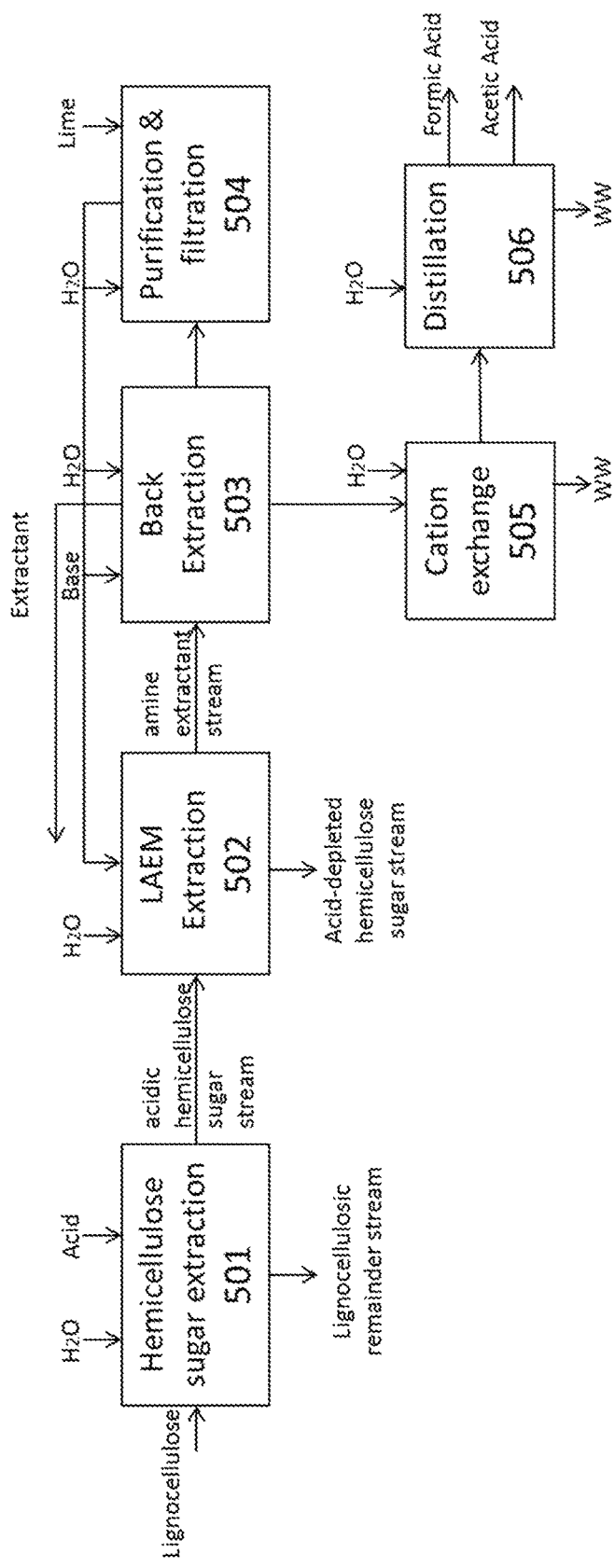
FIG. 5 shows a simplified flow scheme of methods for treating lignocellulose material according to some embodiments of the disclosure.

As shown in FIG. 5, at least a portion of the hemicellulose and impurities are extracted in hemicellulose sugar extraction 501 by liquid extracting (e.g., using an acidic aqueous solution). The hemicellulose sugar extraction 501 may produce an acidic hemicellulose sugar stream and a lignocellulosic remainder stream. The hemicellulose sugar extraction 501 may employ pressure cooking. The acidic hemicellulose sugar stream may be subjected to LAEM extraction 502 using an LAEM containing an amine having at least 20 carbon atoms, resulting in an aqueous stream and an organic stream. Optionally, the LAEM stream is subjected to a water wash followed by a back extraction 503 with a base. At least a portion of the LAEM stream can be subjected to purification and filtration 504 before it is recycled for reuse in LAEM extraction 502. The other part of the stream may be returned directly for reuse in the LAEM extraction 502. The aqueous stream resulting from the back extraction 503 can be subjected to cation exchange 505 and then to distillation 506. Distillation 506 can be conducted to recover acids. Cation exchange 505 and distillation 506 may be optional.

A sugar stream can be contacted with an LAEM comprising an amine and a diluent, to remove at least one mineral acid, at least one organic acid, furfurals, and acid soluble lignins. Optionally, the extraction is a liquid-liquid extraction and is carried out in a device suitable for liquid-liquid extraction, such as a liquid-liquid separation centrifuge. Optionally, the sugar stream is a lignocellulo sic hydrolysate, a hemicellulose sugar stream or a cellulose sugar stream (400-A, see FIG. 4). Optionally, the hydrolysate does not comprise hydrochloric acid.

In certain aspects, the present disclosure provides a method for refining a lignocellulosic hydrolysate. In some examples, the method comprises (a) contacting at least 250 parts of the lignocellulosic hydrolysate with 1 part of a liquid anion exchange medium (LAEM) and (b) recovering at least 225 parts of an aqueous stream, wherein the aqueous stream comprises one or more sugars. Because LAEM is recycled, the ratios above refer to the total volume of the lignocellulosic hydrolysate and LAEM present through all cycles of the process.

The at least 250 parts may comprise at least about 500, at least about 600, at least about 700, at least about 800, at least about 900, at least about 1000, at least about 1500, at least about 2000, at least about 5000, at least about 10,000, or at least about 20,000 parts, such as 500 to 10,000 parts. Preferably, a high percentage of the refined aqueous stream is recovered, such as at least 50%, at least 60%, at least 70%, at least 80%, at least 90%, at least 95%, or at least 99%, such as 50% to 95%. Further, recovering the at least 225 parts of the aqueous stream may comprise at least about 450, at least about 540, at least about 630, at least about 720, at least about 810, at least about 900, at least about 1350, at least about 1800, at least about 4500, at least about 9,000, or at least about 18,000 parts, such as 540 to 9,000 parts.

The contacting and the recovering may occur in a continuous process. Preferably, the LAEM is recycled periodically. For example, new lignocellulosic hydrolysate may be added to 1 part of the LAEM, wherein the 1 part of the LAEM is continuously recycled. The same portion of LAEM may be used to refine the lignocellulosic hydrolysate over many cycles of a continuous process. Once cycle of the process may be repeated at least 5, at least 10, at least 25, at least 50, at least 100, at least 150, at least 200, at least 250, at least 500, at least 750, at least 1000, at least 1500, at least 2000, at least 3000, at least 4000, at least 5000, at least 6000, at least 7000, at least 8000, at least 9000, or at least 10000 times, such as 10 to 9000 times using the same portion of LAEM, wherein the LAEM is neutralized and/or refined after each cycle. In some examples, new LAEM is added to the method to make up for lost LAEM. Optionally, the continuous process comprises the steps of washing, neutralizing, and refining the LAEM. In one cycle of the process, a ratio of LAEM to the lignocellulosic hydrolysate is less than 7:1, less than 6:1, less than 5:1, less than 4:1, less than 3:1, less than 2:1, less than 1:1, or less than 1:2. At any given time, the ratio of LAEM to the lignocellulosic hydrolysate is less than 5:1. The contacting may occur in a liquid-liquid separation centrifuge.

In certain aspects, the present disclosure provides a method for refining a lignocellulosic hydrolysate. In some examples, the method comprises (a) contacting the lignocellulosic hydrolysate with a first portion of a liquid anion exchange medium (LAEM) in a liquid-liquid separation centrifuge to form a mixture, and (b) separating the mixture in the liquid-liquid separation centrifuge into an organic stream and an aqueous stream, wherein the organic stream comprises the LAEM, an acid and an impurity, and wherein the aqueous stream comprises one or more sugars. Optionally, the method further comprises (c) contacting the organic stream with a base, thereby forming a neutralized mixture, and (d) recovering a second portion of an LAEM from the neutralized mixture. In some examples, the lignocellulosic hydrolysate is produced by the hydrolysis of a lignocellulosic biomass, such as sugar cane bagasse or sugar cane leaves.

Preferably, steps (a) and (b) are continuous. For example, steps (a) and (b) may be occurring concurrently, wherein the LAEM and lignocellulosic hydrolysate are continuously introduced to the liquid-liquid separation centrifuge at the same time as organic and aqueous streams are separated from the mixture. Optionally, steps (a) through (d) are continuous. During the repetition of steps (a)-(d), the second portion of an LAEM recovered in step (d) may be reused in step (a) as the first portion of an LAEM when repeating the steps (a)-(d). In some examples, the LAEM may be recycled in a continuous refining loop while new lignocellulo sic hydrolysate is added and the aqueous stream (e.g., a refined hemicellulose sugar stream) is removed. Steps (a) through (d) may be completed within 120 min, within 105 min, within 90 min, within 75 min, within 60 min, within 45 min, within 30 min, or within 15 min. Steps (a) and (b) may be completed within 120 min, within 105 min, within 90 min, within 75 min, within 60 min, within 45 min, within 30 min, within 15 min, or within 5 min, such as 15 min to 90 min.

LAEM may refer to a weak base anion exchanger in the liquid form. Typically, the LAEM may have very low water solubility (e.g. 10 g/100 g of water at 25° C.). The LAEM may comprise an amine that can extract non ionic impurities. During the extraction, the amine may have similar functional groups as a WBA resin. The LAEM may further be dissolved in a solvent (e.g., diluent). Preferably, the diluent may (i) dissolve well both the free tertiary amine $R_3N$ and its bound form $R_3NH^+A^-$; (ii) control viscosity at an industrially useful range, allowing utilization of low cost systems such as mixer-settlers and/or liquid-liquid centrifuges; (iii) contribute further to the capacity of the solvent to extract non-ionic impurities; and/or (iv) allow regeneration of the loaded phase by efficient contact with mineral bases such as caustic or lime.

The LAEM may comprise 10-90% weight/weight, such as 20-60% weight/weight, of one or more amines having at least 20 carbon atoms. The LAEM may comprise 10-90%, such as 10-80%, 10-70%, 10-60%, 10-50%, 10-40%, 20-80%, 20-70%, 20-60%, 20-50%, 20-40%, 15-80%, 15-70%, 15-60%, 15-50%, 15-40%, 15-35%, 25-80%, 25-70%, 25-60%, 25-50%, 25-40%, or 25-35% weight/weight of one or more amines having at least 20 carbon atoms. Such amine(s) can be primary, secondary, or tertiary amines. Tertiary amines can include, for example, tri-laurylamine (TLA; e.g. COGNIS ALAMINE 304 from Cognis Corporation; Tucson Ariz.; USA), tri-octylamine, tri-isooctylamine, tri-caprylylamine and tri-decylamine. Optionally, the LAEM comprises trilaurylamine. Preferably, the LAEM comprises a tertiary amine.

The LAEM may further comprise a diluent. In some examples, the LAEM may comprise at least 10%, at least 20%, at least 30%, at least 40%, at least 50%, at least 60%, at least 70%, at least 80%, or at least 90% weight/weight, such as 55-85% weight/weight, of a diluent. Diluents suitable for use in the LAEM extraction can include an alcohol such as butanol, isobutanol, hexanol, octanol, decanol, dodecanol, tetradecanol, pentadecanol, hexadecanol, octadecanol, eicosanol, docosanol, tetracosanol, and triacontanol. Preferably, the diluent can be a long chain alcohol (e.g. C6, C8, C10, C12, C14, C16 alcohol), or kerosene. Optionally, the diluent is n-hexanol or 2-ethyl-1-hexanol (2E1H). Optionally, the diluent is 2-ethyl-1-hexanol. The diluent can consist essentially of, or consists of, 2-ethyl-1-hexanol. Optionally, the diluent comprises one or more additional components, such as a ketone, an aldehyde having at least 5 carbon atoms, or another alcohol.

Optionally, the LAEM comprises an amine having at least 20 carbon atoms and a diluent (e.g., an alcohol), such as a tertiary amine having at least 20 carbon atoms and an alcohol. In some examples, the LAEM may comprise a tertiary amine having from 20 to 50 carbon atoms and a diluent, wherein the diluent is a $C_{6-12}$ monoalcohol. In some examples, the LAEM can comprise an amine having from 24-40 carbon atoms (e.g., trilaurylamine, trioctylamine, tri-caprylylamine, or tridecylamine) and a diluent, wherein the diluent can be a $C_{6-12}$ monoalcohol (e.g., hexanol, octanol, or 2-ethylhexanol). In some examples, the amine may be trilaurylamine and the diluent may be hexanol or 2-ethylhexanol. Optionally, the LAEM does not comprise an exogenous acid. Acid extracted from a lignocellulo sic hydrolysate may be present in recycled LAEM, though typically no exogenous acid is added to the LAEM by other means.

In some examples, the amine may be trilaurylamine and the diluent may be a $C_{6-12}$ monoalcohol, such as 2-ethyl-1-hexanol. The LAEM can comprise an amine and a diluent in a ratio between 1:10 and 10:1 weight/weight, such as 1:7, 2:7, 3:7, 6:4, 5.5:4.55, 4:7, 5:7, 6:7, 7:7, 5:4, 3:4, 2:4, or 1:4 weight/weight. The ratio of amine and diluent can be any ratio, e.g., between 3:7 and 6:4 weight/weight. In some examples, the LAEM may comprise trilaurylamine and a $C_{6-12}$ monoalcohol in a ratio of 1:7, 2:7, 3:7, 6:4, 5.5:4.55, 4:7, 5:7, 6:7, 7:7, 5:4, 3:4, 2:4, or 1:4 weight/weight. Preferably, the LAEM may comprise trilaurylamine and a $C_{6-12}$ monoalcohol in a ratio of about 3:7 weight/weight, such as a 3:7 weight/weight ratio of trilaurylamine and 2-ethyl-1-hexanol.

Exemplary conversion processes for the purification of the hemicellulose sugar stream (100-A and 400-A) are depicted in FIG. 1 and FIG. 4, including LAEM extraction. In some examples, the organic stream 431-A may comprise the LAEM and at least one impurity. Optionally, at least one impurity may be selected from a mineral acid (e.g., $H_2SO_4$, $H_2SO_3$, and HCl), an organic acid (e.g., acetic acid and formic acid), furfural, hydroxymethylfurfural, and acid soluble lignin. The aqueous stream may comprise hemicellulose sugars. After separation from the organic stream, the aqueous stream is referred to herein as a refined hemicellulose sugar stream (110-P1 and 431-B).

The ratio of the first portion of an LAEM to the lignocellulosic hydrolysate may be less than 10:1, less than 9:1, less than 8:1, less than 7:1, less than 6:1, less than 5:1, less than 4:1, less than 3:1, less than 2:1, or less than 1:1, such as less than 5:1. The lignocellulosic hydrolysate may comprise at least 0.05%, at least 0.1%, at least 0.2%, at least 0.3%, at least 0.4%, at least 0.5%, at least 0.6%, at least 0.7%, at least 0.8%, at least 0.9%, at least 1%, or at least 5% acid weight/weight, such as at least 0.1% to 5% weight/weight of acid. The acid may comprise an inorganic acid and an organic acid.

The organic stream may be washed with water to remove residual sugar from the organic stream, thereby forming a dilute sugar water solution and a washed organic stream. The dilute sugar water solution may be combined with the aqueous stream. The combined stream may comprise at least about 1%, at least about 2%, at least about 3%, at least about 4%, at least about 5%, at least about 6%, at least about 7%, at least about 8%, at least about 9%, at least about 10%, at least about 15%, or at least about 20% wt/wt sugars, such as 2% to 10% wt/wt of sugars.

Typically, a vast majority of sugars may remain in the acid-depleted aqueous stream 431-B, whereas much of the organic and/or inorganic acids (e.g., the acids used in hemicellulose sugar extraction) and impurities can be extracted into the organic stream 431-A. The organic stream 431-A can be contacted with water in a counter current mode to recover any residual sugars absorbed into the organic stream. The organic stream 431-A may contain less than about 5%, about 4%, about 3%, about 2%, about 1%, about 0.8%, about 0.6%, about 0.5%, about 0.4%, about 0.3%, about 0.2%, or less than about 0.1% wt/wt of hemicellulose sugars, such as 0.1% to 4% wt/wt of hemicellulose sugars. The acid-depleted aqueous stream 431-B may contain less than about 5%, about 4%, about 3%, about 2%, about 1%, about 0.8%, about 0.6%, about 0.5%, about 0.4%, about 0.3%, about 0.2%, or less than about 0.1% wt/wt of acid, such as 0.2% to 5% wt/wt of acid. The acid-depleted aqueous stream 431-B can contain less than about 5%, about 4%, about 3%, about 2%, about 1%, about 0.8%, about 0.6%, about 0.5%, about 0.4%, about 0.3%, about 0.2%, or less than about 0.1% wt/wt of amine, such as 0.2% to 4% wt/wt of amine. The acid-depleted aqueous stream 431-B may contain less than about 5%, about 4%, about 3%, about 2%, about 1%, about 0.8%, about 0.6%, about 0.5%, about 0.4%, about 0.3%, about 0.2%, or less than about 0.1% wt/wt of impurities, such as 0.2% to 4% wt/wt of impurities.

The LAEM may comprise 10-90% weight/weight, such as 20-60% weight/weight, of one or more amines having at least 20 carbon atoms. The LAEM may comprise 10-90%, such as 10-80%, 10-70%, 10-60%, 10-50%, 10-40%, 20-80%, 20-70%, 20-60%, 20-50%, 20-40%, 15-80%, 15-70%, 15-60%, 15-50%, 15-40%, 15-35%, 25-80%, 25-70%, 25-60%, 25-50%, 25-40%, or 25-35% weight/weight of one or more amines having at least 20 carbon atoms. Such amine(s) can be primary, secondary, or tertiary amines. Tertiary amines can include, for example, tri-laurylamine (TLA; e.g., COGNIS ALAMINE 304 from Cognis Corporation; Tucson Ariz.; USA), tri-octylamine, tri-isooctylamine, tri-caprylylamine and tri-decylamine. Optionally, the LAEM comprises trilaurylamine.

The LAEM may further comprise a diluent. In some examples, the LAEM can comprise at least 10%, at least 20%, at least 30%, at least 40%, at least 50%, at least 60%, at least 70%, at least 80%, or at least 90% weight/weight, such as 55-85% weight/weight, of a diluent. Diluents suitable for use in the LAEM extraction can include an alcohol such as butanol, isobutanol, hexanol, octanol, decanol, dodecanol, tetradecanol, pentadecanol, hexadecanol, octadecanol, eicosanol, docosanol, tetracosanol, and triacontanol. Preferably, the diluent may be a long chain alcohol (e.g., C6, C8, C10, C12, C14, C16 alcohol), or kerosene. Optionally, the diluent is n-hexanol or 2-ethyl-1-hexanol (2E1H). Optionally, the diluent is 2-ethyl-1-hexanol. The diluent may consist essentially of, or consists of, 2-ethyl-1-hexanol. Optionally, the diluent comprises one or more additional components, such as a ketone, an aldehyde having at least 5 carbon atoms, or another alcohol.

Optionally, the LAEM comprises an amine having at least 20 carbon atoms and a diluent (e.g., an alcohol), such as a tertiary amine having at least 20 carbon atoms and an alcohol. In some examples, the LAEM comprises a tertiary amine having from 20 to 50 carbon atoms and a diluent, wherein the diluent is a $C_{6-12}$ monoalcohol. In some examples, the LAEM can comprise an amine having from 24-40 carbon atoms (e.g., trilaurylamine, trioctylamine, tricaprylylamine, or tridecylamine) and a diluent, wherein the diluent is a $C_{6-12}$ monoalcohol (e.g., hexanol, octanol, or 2-ethylhexanol). In some examples, the amine can be trilaurylamine and the diluent can be hexanol or 2-ethyl-1-hexanol.

In some examples, the amine can be trilaurylamine and the diluent can be a $C_{6-12}$ monoalcohol, such as 2-ethyl-1-hexanol. The LAEM can comprise an amine and a diluent in a ratio between 1:10 and 10:1 weight/weight, such as 1:7, 2:7, 3:7, 6:4, 5.5:4.55, 4:7, 5:7, 6:7, 7:7, 5:4, 3:4, 2:4, or 1:4 weight/weight. The ratio of amine and diluent can be any ratio, e.g., between 3:7 and 6:4 weight/weight. In some examples, the LAEM may comprise trilaurylamine and a $C_{6-12}$ monoalcohol in a ratio of 1:7, 2:7, 3:7, 6:4, 5.5:4.55, 4:7, 5:7, 6:7, 7:7, 5:4, 3:4, 2:4, or 1:4 weight/weight. Preferably, the LAEM may comprise trilaurylamine and a $C_{6-12}$ monoalcohol in a ratio of about 3:7 weight/weight, such as a 3:7 weight/weight ratio of trilaurylamine and 2-ethyl-1-hexanol.

Optionally, the sugar stream 400-A is extracted with the LAEM counter-currently, e.g., the sugar stream 400-A flows in an opposite direction to the flow of the LAEM. The countercurrent extraction can be carried out in any suitable device. The suitable device may be selected from the group consisting of a centrifuge, a mixer-settler device, a stirred tank, and a column, or any combination thereof. The centrifuge may be a liquid-liquid separation centrifuge.

The liquid-liquid centrifuge may be a Rousselet Robatel model BXP 190, with a nominal capacity of 150 gpm. The lignocellulosic hydrolysate and the LAEM, having a different density than that of the lignocellulosic hydrolysate may be fed into a mixing chamber. The mixing chamber may be located on the bottom of the centrifuge. The two liquids can be typically mixed by a rotating agitator disc. Efficient mixing can result in a large interfacial area between the two liquids to generate maximum mass transfer of the solutes.

A turbine may be typically located on the bottom of the rotating bowl. The turbine can aspirate the lignocellulo sic hydrolysate and LAEM dispersion into the centrifuge bowl. The rotating bowl can be capable of generating a centrifugal force that separates the liquids. The heavier liquid may migrate on the outer portion of the bowl, while the light liquid can migrate to the inner portion of the bowl. A heavy phase weir can regulate the position of the liquid/liquid interphase. A selection of interchangeable heavy phase weirs with different dia-meters may be available to accommodate a wide range of density ratios. The heavy phase can underflow into a static receiving chamber and the light phase can overflow to a separate static receiving chamber.

Gravity can discharge the liquids to the next BXP centrifugal extractor or to downstream equipment. During multi-stage extraction processes, the liquid-liquid centrifuges can be installed in series to provide the required number of stages. Inter-stage pumps may not be required between the extractors. The external inter-stage piping can allow for feeds to enter into or routed out of the extraction process, for example, main extraction, scrubbing, back extraction, as required for optimum flexibility.

The refining method can be conducted at any temperature at which the amine is soluble, preferably at 50-70° C. In some methods, the temperature may be at least about 40° C., about 45° C., about 50° C., about 55° C., about 60° C., about 65° C., about 70° C., about 75° C., or at least about 80° C. Optionally, the refining method comprises more than one extraction step (e.g., 2, 3, or 4 steps). The ratio of the first portion of the LAEM stream (organic stream) to the hemicellulose sugar stream (aqueous stream) can range from about 0.5:1 to about 5:1 weight/weight, such as about 0.5:1, about 1:1, about 1.5:1, about 2:1, about 2.5:1, about 3:1, about 3.5:1, about 4:1, about 4.5:1, or about 5:1. In some examples, the ratio of the organic stream to the aqueous stream is about 1.5-3.0:1 weight/weight.

After contacting the hemicellulose sugar stream with the LAEM, the resulting mixture can be separated into an organic stream (i.e., the organic phase) comprising the LAEM and at least one impurity and a refined hemicellulose sugar stream (i.e., the aqueous phase). At least a portion of organic acids or inorganic acids (e.g., the acids used in hemicellulose sugar extraction) and other impurities may be extracted into the organic stream. Surprisingly, the refining process can efficiently cope with added amounts of impurities resulting from the hydrolysate of sugar cane leaves. In some examples, leaves may contain at least about 1, at least about 2, at least about 3, at least about 4, at least about 5, at least about 6, or at least about 7 times higher the amounts of protein than that in bagasse. Protein may hydrolyze to amino acids along with the saccharide polymer.

In some examples, the organic stream may be contacted with an aqueous stream in a counter current mode to recover any residual sugars absorbed into the organic stream. The organic stream may comprise the LAEM, an organic acid, an inorganic acid, amino acids, and other impurities. The organic stream may comprise less than 5%, less than 4%, less than 3%, less than 2%, less than 1%, less than 0.8%, less than 0.6%, less than 0.5%, less than 0.4%, less than 0.3%, less than 0.2%, less than 0.1%, less than 0.05%, less than 0.02% or less than 0.01% weight/weight hemicellulose sugars, such as 0.001% to 0.01% hemicellulose sugars. The organic stream may comprise organic acids (such as acetic acid, formic acid, levulinic acid), inorganic acids (such as sulfuric acid), furfural, protein, amino acids, and ash. The organic stream may comprise at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, or at least about 5% weight/weight of organic acids, such as 0.1% to 3% of organic acids. The organic stream may comprise at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, or at least about 2% weight/weight of acetic acid, such as 0.1% to 1% of acetic acid. The organic stream may comprise at least about 0.001%, at least about 0.002%, at least about 0.003%, at least about 0.004%, at least about 0.005%, at least about 0.006%, at least about 0.007%, at least about 0.008%, at least about 0.009%, at least about 0.01%, at least about 0.02%, or at least about 0.05% weight/weight of formic acid, such as 0.001% to 0.05% of formic acid. The organic stream may comprise at least about 0.001%, at least about 0.002%, at least about 0.003%, at least about 0.004%, at least about 0.005%, at least about 0.006%, at least about 0.007%, at least about 0.008%, at least about 0.009%, at least about 0.01%, at least about 0.02%, at least about 0.05%, or at least about 0.1% weight/weight of levulinic acid, such as 0.001% to 0.1% of levulinic acid. The organic stream may comprise at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, or at least about 5% weight/weight of inorganic acids, such as 0.1% to 3% of inorganic acids. The organic stream may comprise at least about 0.1%, at least about 0.2%, at least about 0.3%, at least about 0.4%, at least about 0.5%, at least about 0.6%, at least about 0.7%, at least about 0.8%, at least about 0.9%, at least about 1%, or at least about 2% weight/weight of sulfuric acid, such as 0.1% to 1% of sulfuric acid. The organic stream may comprise at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, or at least about 5% weight/weight of furfurals, such as 0.1% to 3% of furfurals. The organic stream may comprise at least about 0.001%, at least about 0.002%, at least about 0.005%, at least about 0.01%, at least about 0.02%, at least about 0.3%, at least about 0.4%, at least about 0.5%, at least about 0.6%, at least about 0.7%, at least about 0.8%, or at least about 0.9% weight/weight of methanol, such as 0.001% to 0.1% of methanol. The organic stream may comprise at least about 1.0%, at least 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.3%, at least about 2.4% or at least about 2.5% weight/weight of acid soluble lignin, such as 1.5% to 2.5% of acid soluble lignin. The organic stream may comprise at least about 0.001%, at least about 0.002%, at least about 0.003%, at least about 0.004%, at least about 0.005%, at least about 0.006%, at least about 0.007%, at least about 0.008%, at least about 0.009%, at least about 0.01%, at least about 0.1%, or at least about 0.2%, weight/weight of amino acids, such as 0.001% to 0.2% of amino acids. The organic stream may comprise at least about 0.01%, at least about 0.02%, at least about 0.03%, at least about 0.04%, at least about 0.05%, at least about 0.06%, at least about 0.07%, at least about 0.08%, at least about 0.09%, at least about 0.1%, at least about 0.2%, at least about 0.3%, at least about 0.4%, or at least about 0.5% weight/weight of ash, such as 0.01% to 0.3% of ash. The organic stream may comprise 0.1% to 1% of acetic acid, 0.001% to 0.05% of formic acid, 0.001% to 0.1% levulinic acid, 0.1% to 1% sulfuric acid, 0.1% to 3% furfural, 0.001% to 1% amino acids, and 0.01% to 3% ash. The organic stream may comprise 0.001% to 0.01% hemicellulose sugars, 0.1% to 3% of organic acids, 0.1% to 1% of acetic acid, 0.001% to 0.05% of formic acid, 0.001% to 0.1% levulinic acid, 0.1% to 3% of inorganic acids, 0.1% to 1% sulfuric acid, 0.1% to 3% furfural, 0.001% to 0.1% of methanol, 1.5% to 2.5% of acid soluble lignin, 0.001% to 0.2% amino acids, and 0.01% to 0.3% ash.

In some examples, the refined hemicellulose sugar stream comprises less than 3%, less than 2%, less than 1%, less than 0.8%, less than 0.6%, less than 0.5%, less than 0.4%, less than 0.3%, less than 0.2%, or less than 0.1% weight/weight acid, such as 0.01% to 3% weight/weight of acid. In some examples, the aqueous stream (refined hemicellulose sugar stream) may comprise less than 400 ppm, less than 300 ppm, less than 200 ppm, less than 100 ppm, less than 50 ppm, or less than 10 ppm of calcium, such as 10 ppm to 300 ppm of calcium. In some examples, the refined hemicellulose sugar stream may comprise less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight of an amine having at least 20 carbon atoms, such as 0.01% to 4% of an amine. In some examples, the refined hemicellulose sugar stream may comprise less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight of an impurity, such as 0.1% to 4% of an impurity, wherein the impurity is selected from ash, acid soluble lignin, furfural, fatty acids, organic acids such as acetic acid and formic acid, mineral acids such as hydrochloric acid and sulfuric acid, furfural, hydroxymethylfurfural, methanol, proteins, amino acids, glycerol, sterols, rosin acid, and waxy materials. In some examples, acid may not be recovered by distillation. Preferably, the LAEM does not comprise an additional oil soluble organic acid, other than the extracted acid composition.

The refined hemicellulose sugar stream may comprise less than 2000 ppm, less than 1500 ppm, less than 1000 ppm, less than 800 ppm, less than 600 ppm, less than 400 ppm, less than 200 ppm, less than 100 ppm, or less than 50 ppm of acetic acid, such as 50 ppm to 1500 ppm of acetic acid. The refined hemicellulose sugar stream may comprise less than 2000 ppm, less than 1500 ppm, less than 1000 ppm, less than 800 ppm, less than 600 ppm, less than 400 ppm, less than 200 ppm, less than 100 ppm, or less than 50 ppm of formic acid, such as 50 ppm to 1500 ppm of formic acid. The refined hemicellulose sugar stream may comprise less than 2000 ppm, less than 1500 ppm, less than 1000 ppm, less than 800 ppm, less than 600 ppm, less than 400 ppm, less than 200 ppm, less than 100 ppm, or less than 50 ppm of sulfuric acid, such as 50 ppm to 1500 ppm of sulfuric acid. The refined hemicellulose sugar stream may comprise less than 2000 ppm, less than 1500 ppm, less than 1000 ppm, less than 800 ppm, less than 600 ppm, less than 400 ppm, less than 200 ppm, less than 100 ppm, or less than 50 ppm of hydrochloric acid, such as 50 ppm to 1500 ppm of hydrochloric acid. The refined hemicellulose sugar stream may comprise less than 700 ppm, less than 600 ppm, less than 500 ppm, less than 400 ppm, less than 300 ppm, less than 200 ppm, less than 100 ppm, or less than 50 ppm of furfural, such as 200 ppm to 600 ppm of furfural. In some examples, the refined hemicellulose sugar stream comprises less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight ash, such as 0.1% to 4% of ash. In some examples, the refined hemicellulose sugar stream comprises less than 2000 ppm, less than 1500 ppm, less than 1000 ppm, less than 800 ppm, less than 600 ppm, less than 400 ppm, less than 200 ppm, less than 100 ppm, or less than 50 ppm of nitrogen, such as 50 ppm to 1500 ppm of nitrogen. In some examples, the refined hemicellulose sugar stream comprises less than 2000 ppm, less than 1500 ppm, less than 1000 ppm, less than 800 ppm, less than 600 ppm, less than 400 ppm, less than 200 ppm, less than 100 ppm, or less than 50 ppm of protein, such as 50 ppm to 1500 ppm of protein. In some examples, the refined hemicellulose sugar stream comprises less than 2000 ppm, less than 1500 ppm, less than 1000 ppm, less than 800 ppm, less than 600 ppm, less than 400 ppm, less than 200 ppm, less than 100 ppm, or less than 50 ppm of amino acids, such as 50 ppm to 1500 ppm of amino acids. The refined hemicellulose sugar stream may comprise 50 ppm to 1500 ppm of acetic acid, less than 1500 ppm of formic acid, 50 ppm to 1500 ppm of sulfuric acid, less than 1500 ppm of hydrochloric acid, 200 ppm to 600 ppm of furfural, less than 4% weight/weight of ash, less than 1500 ppm of nitrogen, less than 1500 ppm of protein, and less than 1500 ppm of amino acids. The refined hemicellulose sugar stream may comprise 0.01% to 3% weight/weight of acid, 10 ppm to 300 ppm of calcium, 0.01% to 4% of an amine, 0.1% to 4% of an impurity, 50 ppm to 1500 ppm of acetic acid, less than 1500 ppm of formic acid, 50 ppm to 1500 ppm of sulfuric acid, less than 1500 ppm of hydrochloric acid, 200 ppm to 600 ppm of furfural, less than 4% weight/weight of ash, less than 1500 ppm of nitrogen, less than 1500 ppm of protein, and less than 1500 ppm of amino acids.

In some examples, the organic stream may be converted to the recycled LAEM stream. The recycled LAEM stream may comprise trilaurylamine, 2E1H, an organic acid, an inorganic acid, amino acids, and other impurities. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, at most about 0.02%, at most about 0.03%, at most about 0.04%, at most about 0.05%, at most about 0.06%, at most about 0.07%, at most about 0.08%, at most about 0.09% or at most about 0.1% weight/weight of organic acids, such as 0.001% to 0.1% of organic acids. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, at most about 0.02%, at most about 0.03%, at most about 0.04%, at most about 0.05%, at most about 0.06%, at most about 0.07%, at most about 0.08%, at most about 0.09%, or at most 0.1% weight/weight of acetic acid, such as 0.001% to 0.1% of acetic acid. The recycled LAEM stream may comprise at most about 0.001%, at most about 0.002%, at most about 0.003%, at most about 0.004%, at most about 0.005%, at most about 0.006%, at most 0.007%, at most about 0.008%, at most about 0.009%, at most about 0.01%, or at most about 0.02% weight/weight of formic acid, such as 0.001% to 0.01% of formic acid. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, or at most about 0.02% weight/weight of levulinic acid, such as 0.001% to 0.01% of levulinic acid. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, at most about 0.02%, at most about 0.03%, at most about 0.04%, or at most about 0.05% weight/weight of inorganic acids, such as 0.001% to 0.03% of inorganic acids. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, or at most about 0.02% weight/weight of sulfuric acid, such as 0.001% to 0.01% of sulfuric acid. The recycled LAEM stream may comprise at most about 0.01%, at most about 0.02%, at most about 0.03%, at most about 0.04%, at most about 0.05%, at most about 0.06%, at most about 0.07%, at most about 0.08%, at most about 0.09%, at most about 0.1%, at most about 0.2%, at most about 0.3%, at most about 0.4%, or at most about 0.5% weight/weight of furfurals, such as 0.05% to 0.3% of furfurals. The organic stream may comprise at least about 0.001%, at least about 0.002%, at least about 0.005%, at least about 0.01%, at least about 0.02%, at least about 0.3%, at least about 0.4%, at least about 0.5%, at least about 0.6%, at least about 0.7%, at least about 0.8%, or at least about 0.9% weight/weight of methanol, such as 0.001% to 0.1% of methanol. The recycled LAEM stream may comprise at least about 1.0%, at least 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.3%, at least about 2.4% or at least about 2.5% weight/weight of acid soluble lignin, such as 1.5% to 2.5% of acid soluble lignin. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, at most about 0.02%, at most about 0.03%, at most about 0.04%, or at most about 0.05% weight/weight of amino acids, such as 0.001% to 0.03% of amino acids. The recycled LAEM stream may comprise at most about 0.001%, at most about 0.002%, at most about 0.003%, at most about 0.004%, at most about 0.005%, at most about 0.006%, at most about 0.007%, at most about 0.008%, at most about 0.009%, at most about 0.01%, at most about 0.02%, at most about 0.03%, at most about 0.04%, or at most about 0.05% weight/weight of ash, such as 0.001% to 0.03% of ash. The recycled LAEM stream may comprise 0.001% to 0.1% of acetic acid, 0.001% to 0.01% of formic acid, 0.001% to 0.01% levulinic acid, 0.001% to 0.01% sulfuric acid, 0.05% to 0.3% furfural, 0.001% to 0.03% amino acids, and 0.001% to 0.03% ash. The recycled LAEM stream may comprise 0.001% to 0.1% of organic acids, 0.001% to 0.1% of acetic acid, 0.001% to 0.01% of formic acid, 0.001% to 0.01% levulinic acid, 0.001% to 0.03% of inorganic acids, 0.001% to 0.01% sulfuric acid, 0.05% to 0.3% furfural, 0.001% to 0.1% of methanol, 1.5% to 2.5% of acid soluble lignin, 0.001% to 0.03% amino acids, and 0.001% to 0.03% ash.

The refined hemicellulose sugar stream can be further purified. For example, residual diluent in the refined hemicellulose sugar stream can be removed using a packed distillation column. The distillation can remove at least 70%, at least 80%, at least 90%, or at least 95% of residual diluent in the refined hemicellulose sugar stream. In some examples, the refined hemicellulose sugar stream can be contacted with a strong acid cation (SAC) exchanger (433) to remove residual metallic cations and residual amines, then optionally contacted with a weak base anion (WBA) exchanger (434) to remove excess protons. Optionally, the refined hemicellulose sugar stream is purified using a distillation column (e.g., a packed distillation column) followed by a strong acid cation exchanger. In some examples, the refined hemicellulose sugar stream may be contacted with a weak base anion (WBA) exchanger to remove excess protons. The refined hemicellulose sugar stream can be pH adjusted, optionally after contacting the stream with a SAC exchanger and/or WBA exchanger. The refined hemicellulose sugar stream can be distilled or evaporated, then further polished by contacting with a SAC resin, a WBA resin, and a MB resin, and optionally concentrated by evaporation. In some examples, the refined hemicellulose sugar stream can be evaporated (435) to 20-80% weight/weight dissolved sugars, such as 25-65% or 30-40% weight/weight dissolved sugars, thereby forming a concentrated sugar solution (436). The evaporation may be conducted in any conventional evaporator, e.g., a multiple effect evaporator or a mechanical vapor recompression (MVR) evaporator.

Residual solvent present in the hemicellulose sugar stream or concentrated sugar solution can also be removed by evaporation. For example, a solvent that forms a heterogeneous azeotrope with water can be separated and optionally returned to the solvent cycle. Optionally, the refined hemicellulose sugar stream can be contacted with activated carbon to remove residual organic impurities. The refined hemicellulose sugar stream may also be contacted with mixed bed resin system to remove any residual ions or color bodies.

The LAEM stream 431-A can be back-extracted with an aqueous solution containing a base (e.g., sodium hydroxide, sodium carbonate, and magnesium hydroxide) (see, e.g., process denoted in FIG. 4 by the number 450). Base may be added as an aqueous suspension or solution. A portion of the solvent can be further purified using a lime solution (e.g., calcium oxide, calcium hydroxide, calcium carbonate, or a combination thereof) (see, e.g., process denoted in FIG. 4 by the number 460) and the purified solvent can be recycled back to the LAEM extraction 431.

Optionally, prior to contacting the organic stream with a base 450, the organic stream 431-A is washed with water to recover any sugars in the stream to form a dilute sugar water solution. Typically, after the washing, the organic stream 431-A may be less than 5%, 2%, 1%, 0.5%, 0.2%, 0.1%, or less than 0.05% of sugars, such as 0.1% to 2% of sugars.

The base may be added as an aqueous solution or suspension. Optionally, the base is lime. The base can be a solution or suspension comprising lime, NaOH, $Na_2CO_3$, $Mg(OH)_2$, MgO, or $NH_4OH$. Optionally, the concentration of the base is about 1-20% weight/weight, preferably 4-10% weight/weight. Preferably, the base can produce a soluble salt after contacting acid in the acid-loaded organic stream. Preferably, base can be present in 2-10% excess over the stoichiometric equivalent of acid in the organic stream. The pH of the neutralized mixture may be between 5-8, such as pH 6-7. For example, the pH may be about 5.5, about 5.7, about 6.0, about 6.5, about 6.7, about 7.0, or about 7.5.

Contacting the organic stream with a base (e.g., back extraction) 450 can be carried out in any device, such as a centrifuge, a mixer-settler, stirred tanks, columns, or any other equipment suitable for this mode of back extraction. Preferably, the organic stream can be added to the base in a liquid-liquid separation centrifuge. Back extraction can result in removal of at least 90% of the mineral acid and at least 80% of the organic acid from the organic phase. In some examples, back extraction may remove at least 90%, such as at least 95%, of acids from the organic phase. In some examples, a fraction of the organic stream, typically 5-25% of the total weight of the organic stream, can be diverted to a deep cleaning process. The deep cleaning process may comprise contacting the organic stream with a base, such as sodium hydroxide, potassium hydroxide, and/or calcium oxide. The pH of the deep cleaning process may be at least 10, at least 11, at least 12, at least 13, or at least 14, such as 11 to 14. Optionally, this mixture comprising a fraction of the organic stream and base is combined with the remaining organic stream.

Optionally, the back extraction 450 is carried out in multiple reactors. In one example, back extraction 450 is carried out in 4 reactors. In the first reactor, an amount of base equivalent to that of carboxylic acid can be added, and only the carboxylic acids may be extracted from the LAEM to produce a solution of the corresponding salts (e.g., sodium salt). In the second reactor, the mineral acid may be extracted from the LAEM. The streams coming out of each reactor may be treated separately to allow recovery of the organic acids. Optionally, the aqueous streams coming out of the back extraction steps can be combined. Typically, the combined stream may contain at least 3% of the anion of the mineral acid (e.g., sulfate ion if sulfuric and/or sulfurous acids were used in hemicellulose sugar extraction 100), 0.2-3% acetic acid, and lower concentrations of other organic acids. The aqueous stream can contain low concentration of the diluent, typically less than 0.5%, depending on the solubility of the diluent used in water. Preferably, the aqueous stream coming out of back extraction can be kept to allow segregation of chemicals present in these streams. In one example, $Ca^{2+}$ and $SO_4^{2-}$, which are deleterious to anaerobic digestion, may be routed separately to aerobic treatment.

The diluent may be removed from the aqueous phase by distillation. In some examples, the diluent can form a heterogeneous azeotrope with water that has a lower boiling point than the diluent alone, thus the energy required to distill off the diluent is significantly reduced due to the vast excess of water over the diluent. The distilled diluent can be recovered and recycled for further use. The diluent-stripped aqueous phase may be directed to the waste treatment unit of the plant.

The organic stream, now neutralized after acid removal, can be washed with water to remove salts remaining from the back extraction. Optionally, the neutralized organic stream is washed with blended extractants that can partially saturate with water, such as certain alcohols. The wash stream may be combined with the back extraction aqueous stream. In some examples, a fraction of the washed organic stream, typically 5-25% of the total weight of the organic stream, can be diverted to the purification and filtration step (see also, process 460 in FIG. 4). The remaining organic stream (i.e., a second portion of an LAEM) can be recycled to the refining method denoted as 502 (referred to as LAEM extraction in FIG. 5). The second portion of the LAEM may be washed with water, thereby forming a washed LAEM. The portion of the washed organic stream (LAEM) may be less than 30%, less than 25%, less than 20%, less than 15%, less than 10%, or less than 5% by weight of the washed organic stream, such as 10% to 25% by weight of the washed organic stream. The washed LAEM may be contacted with a second base. The pH of the base may be at least 10, at least 11, at least 12, at least 13, or at least 14, such as 11 to 13. The neutralized organic stream is also referred to herein as a second portion of an LAEM. During the continuous process of refining the lignocellulosic hydrolysate, the second portion of an LAEM recovered from the neutralized mixture may be reused when contacting the lignocellulo sic hydrolysate with a first portion of an LAEM. The continuous process may be repeated at least 20, at least 25, at least 30, at least 35, at least 40, at least 45, at least 50, at least 55, at least 60, at least 65, or at least 70 times in a day, such as 25 to 65 times a day. The volume of the second portion of an LAEM after repeating is at least about 50%, at least about 55%, at least about 60%, at least about 65%, at least about 70%, at least about 75%, at least about 80%, at least about 85%, at least about 85%, at least about 90% or at least about 97% of the volume, such as 55% to 85% of the volume of the first portion of an LAEM before the repeating.

The fraction diverted to the purification step (504 in FIG. 5; process 460 in FIG. 4) can be treated with a suitable base, such as a 5%, 10%, 15%, 20%, 25% weight/weight mixture of lime, sodium hydroxide or potassium hydroxide. The solvent to base suspension ratio can be in the range of 1:1 to 10:1, such as 4:1-10:1, 4:1-5:1, 5:1-6:1, 6:1-7:1, 7:1-8:1, 8:1-9:1, or 9:1-10:1. Treatment may be conducted in any suitable device, e.g., a thermostatic mixed tank. The solution can be heated for at least 1 hour at 60-100° C., such as 80-90° C. Base, such as lime, can react with residual organic acids and esters of organic acids and adsorb organic impurities present in the organic phase, such as acid soluble lignin and furfurals, as visualized by a change of color from dark to light. The contaminated base and impurities can be filtered or centrifuged to recover the purified organic stream, which is washed with water and recycled back to the hydrolysate refining process (502 in FIG. 5; process 431 in FIG. 4). The aqueous stream may be diverted to other aqueous waste streams. Any solid cake that may be formed by the base reaction may be used in the waste water treatment plant as a neutralization salt for residual acids, such as those produced from ion exchange regenerations.

The back extraction aqueous stream may contain salts of the organic acids. This stream can be contacted with a cation exchanger to convert all salts to their respective organic acids (see, e.g., the processes denoted as 505 in FIG. 5). Alternatively, the organic acids can be converted to the acid form by acidifying the solution with a strong mineral acid. The acidified stream can be distilled to harvest formic acid and acetic acid (e.g., process 506 in FIG. 5). Remaining aqueous streams may be diverted to waste.

In one aspect, the disclosure provides a system for refining a lignocellulo sic hydrolysate. In some examples, the system comprises (a) a hydrolysate refining unit comprising a first inlet to receive a lignocellulo sic hydrolysate stream, a second inlet to receive a recycled LAEM stream, a first outlet to release an organic stream, and a second outlet to release an aqueous stream, and (b) a neutralization unit in fluid communication with the hydrolysate refining unit, wherein the neutralization unit comprises an inlet to receive the organic stream and a second inlet to receive a base, wherein the neutralization unit is configured to convert the organic stream to the recycled LAEM stream, and further wherein the neutralization unit comprises a first outlet to release the recycled LAEM stream in fluid communication with the second inlet of the hydrolysate refining unit.

The system may comprise a hydrolysate refining unit, wherein the hydrolysate refining unit is configured to receive a lignocellulosic hydrolysate stream and a recycled LAEM, and wherein the LAEM removes impurities from the hemicellulose sugar stream to produce a refined hemicellulose sugar stream. Optionally, the lignocellulosic hydrolysate stream is extracted with the LAEM counter-currently, e.g., the lignocellulosic hydrolysate stream flows in a direction opposite to the flow of the LAEM. The hydrolysate refining unit may comprise a mixer-settler device, a stirred tank, a liquid-liquid separation centrifuge, a column, or a combination thereof. Optionally, the mixer-settler device, stirred tank, liquid-liquid separation centrifuge, or column is equipped with a liquid feed device to receive the lignocellulosic hydrolysate stream. The hydrolysate refining unit may be a centrifuge, such as a liquid-liquid separation centrifuge. The hydrolysate refining unit may comprise at least one liquid-liquid separation centrifuge, such as at least 2 liquid-liquid separation centrifuges. Optionally, the hydrolysate refining unit comprises at least 2, at least 3, at least 4, or at least 5 liquid-liquid separation centrifuges. The hydrolysate refining unit can be equipped with an inlet to receive the LAEM. Optionally, both mixing of the hydrolysate stream with the LAEM stream and separation may be conducted in a liquid-liquid separation centrifuge. In some examples, the hydrolysate stream and the LAEM stream are premixed and fed to the centrifuge as a mixture through a single inlet. Liquid-liquid separation centrifuges are commercially available from various suppliers, including, for example, Rousselet Robatel Inc. and US Centrifuge Systems LLC. The refining unit can be maintained at any temperature at which the amine is soluble, such as 50-70° C. The ratio of the LAEM stream (organic stream) to the lignocellulo sic hydrolysate stream (aqueous stream) can range from about 0.5:1 to about 10:1 weight/weight, such as about 3:1, about 3.5:1, about 4:1, about 4.5:1, about 5:1, about 5.5:1, or about 6:1. In some examples, the ratio of the organic stream to the aqueous stream is between about 3:1 to about 5:1 weight/weight. In some examples, the hydrolysate refining unit can further comprise column or batch units for contacting the lignocellulo sic hydrolysate stream with ion exchange resins or activated carbon to further polish the aqueous solution. In some examples, the second outlet of the hydrolysate refining unit may be in fluid communication with a fermentation unit, wherein the fermentation unit can be configured to convert sugars in the aqueous stream to fermentation products.

The hydrolysate refining unit may be in fluid communication with an LAEM refining unit. The LAEM refining unit can comprise an inlet to receive the organic stream. The LAEM refining unit may comprise an outlet to release an entrained sugar stream and a loaded organic stream. The LAEM refining unit can comprise a centrifuge or a static mixer and a decanter centrifuge.

The neutralization unit may comprise a liquid-liquid separation centrifuge. The neutralization unit can comprise a mixing tank configured to an organic stream and base. The neutralization unit can be in fluid communication with a cleaning unit.

The cleaning unit may comprise an inlet to receive at least 5% of the recycled LAEM stream. In some examples, the cleaning unit can be configured to contact the recycled LAEM stream with a base, thereby forming a mixture. The cleaning unit can comprise an outlet to release the mixture into the neutralization unit.

The present systems and processes are designed to be used and performed at industrially relevant scales. Processes described herein for refining lignocellulosic hydrolysates may be performed using industrially available means and machines that can support high production rates at low cost, while maintaining high purification power. A process of the present disclosure may be scaled to a size that allows refining of at least 1,000 tons of lignocellulosic hydrolysate per annum, or more. Optionally, this enables production of at least 7,000 tons of purified xylose per annum, or more.

A continuous process described herein may comprise at least 3 extraction steps: (i) extraction of mineral acid, organic acid and impurities by contacting the lignocellulosic hydrolysate with a first portion of a liquid anion exchange medium (LAEM) and separating the contacted mixture into an aqueous stream and a loaded organic stream; (ii) back extracting entrained sugar from the loaded organic stream by contacting the organic stream comprising the LAEM, the acids and the impurities with water, and separating the resultant mixture into an aqueous stream and a loaded organic stream; and (iii) regenerating the LAEM by contacting the loaded organic stream comprising the LAEM, the acids and the impurities with a base solution or suspension and separating the resultant mixture into a waste aqueous stream comprising the anions of the acids and impurities and an organic stream comprising the regenerated LAEM. The reagents may be continuously recycled.

Each such step may be performed in a liquid-liquid separation centrifuge. The liquid-liquid separation centrifuge may comprise a mixing section at the inlet and a separating unit in the rotating section. Optionally, the liquid-liquid separation centrifuge is used in some, but not all, of the steps. The other steps may be performed using different mixing and separation apparatuses. Preferably, the step of contacting a lignocellulosic hydrolysate may be conducted using a liquid-liquid separation centrifuge to afford high efficiency at high throughput. Furthermore, this extraction may be done in a countercurrent mode. In other instances, this extraction may be achieved in a single stage mode. Optionally, at least one line of the first step of extraction, for example, at least 2 lines of the first extraction step, can feed a single line of the solvent recycling contacts. The second step of extraction (i.e., back extracting entrained sugar) may be conducted in a liquid-liquid separation centrifuge. The second step of extraction may be conducted by mixing the loaded organic stream with wash water in a static mixer and separating in a centrifuge, for example a decanter centrifuge. Optionally, the third step of extraction (i.e., regenerating the LAEM) is conducted by mixing the loaded organic stream with a base suspension or solution in a mixing tank and separating the mixture in a centrifuge, for example a liquid-liquid separation centrifuge. Examples of industrial setups for refining lignocellulo sic hydrolysates in accordance with the disclosed methods are presented schematically in FIGS. 7, 8 and 9.

Figure 7:
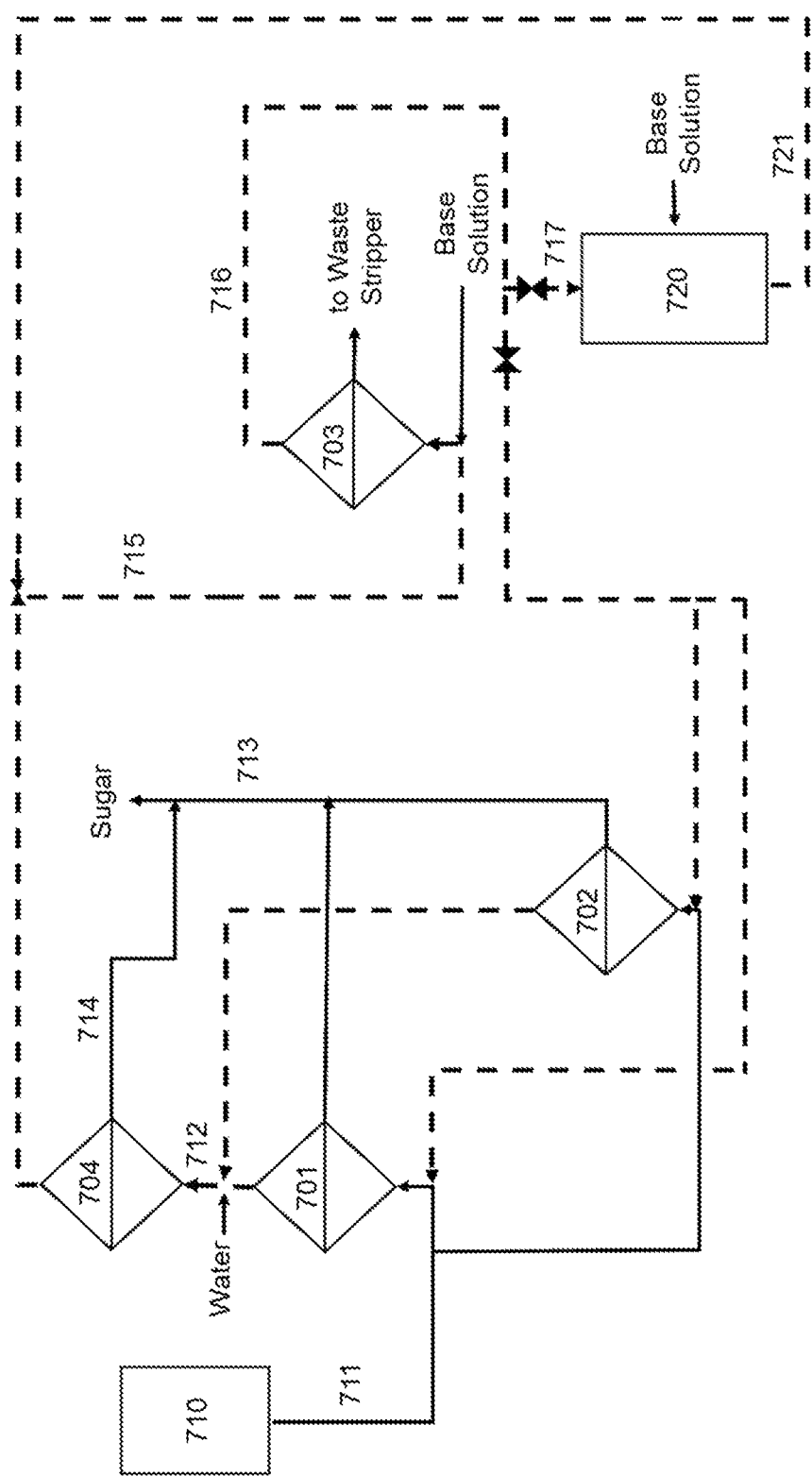
FIG. 7 depicts a scheme of an industrial production setup for refining a lignocellulosic hydrolysate according to certain embodiments of the present disclosure.

FIG. 7 depicts a scheme of an industrial production setup using only liquid-liquid separation centrifuges for all extraction steps. The feed hydrolysate may be held in a feed tank 710, after separating the hydrolysate from solids and contacting the hydrolysate with a strong acid cation exchange resin (SAC). Stream 711 can feed the hydrolysate into two hydrolysate refining units 701 and 702. Each hydrolysate refining unit may also be fed with the organic stream 716 (i.e., the LAEM). The light phase, i.e., the loaded organic phase of both centrifuges, may be combined into a single stream 712, where it is optionally fed together with wash water into the LAEM refining unit 704 to back-extract entrained sugars. Aqueous stream 713, comprising the refined sugar from both centrifuges 701 and 702, may be combined with aqueous stream 714 to yield the sugar solution stream that is sent for polishing and concentrating as disclosed in PCT Appl. No. PCT/US2013/039585 and PCT/US2016/012384, incorporated herein by reference. The hydrolysate refining unit may be in fluid communication with an LAEM refining unit. The LAEM refining unit may comprise an inlet to receive an organic stream. The organic phase from the hydrolysate refining unit may be fed together with wash water into an LAEM refining unit to back-extract entrained sugars. The LAEM refining unit may comprise an outlet to release an entrained sugar stream and a loaded organic stream. The LAEM refining unit may comprise a centrifuge or a static mixer and a decanter centrifuge.

The organic stream 715 that comes out of the LAEM refining unit 704 may be sent to the neutralization unit 703, where it is mixed with an aqueous base solution to neutralize the LAEM. The neutralization unit may comprise a liquid-liquid separation centrifuge. The neutralization unit may be in fluid communication with a cleaning unit. The aqueous phase coming out of the neutralization unit 703 may carry the removed acids and impurities, and may be sent to the waste treatment part of the plant. Stream 716 of regenerated LAEM can be sent back to centrifuges 701 and 702 for further use. The cleaning unit 720 may comprise an inlet to receive at least 1%, 2%, 3%, 5%, 10%, 15%, 20%, or at least 25% of the recycled LAEM stream 716 that is diverted to stream 717. The cleaning unit may be configured to contact the recycled LAEM stream with a base, thereby forming a mixture. The cleaning unit may comprise an outlet to release the organic and aqueous phase mixture, stream 721, into the neutralization unit 703, together with stream 715.

Figure 8:
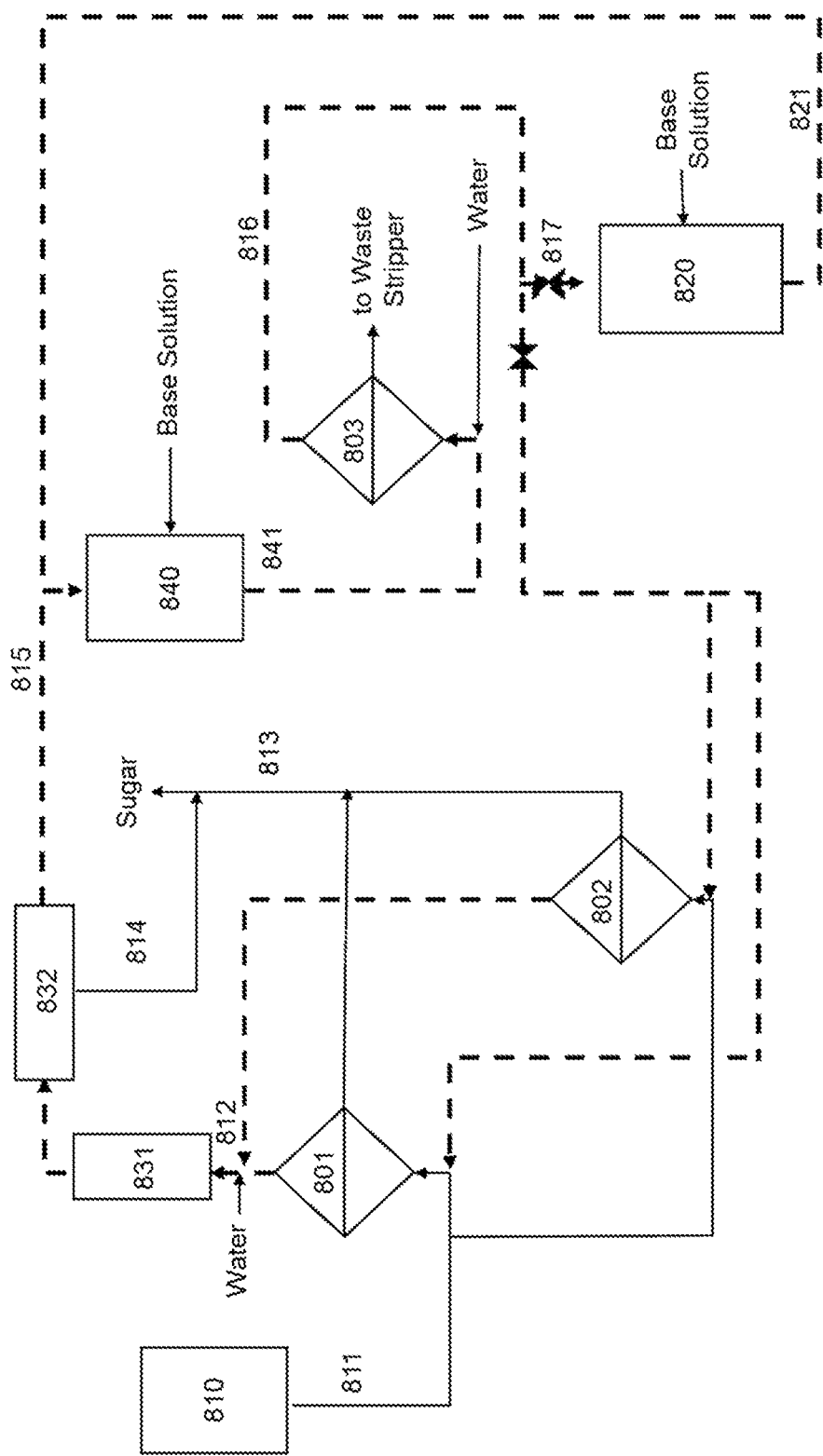
FIG. 8 depicts a scheme of an industrial production setup for refining a lignocellulosic hydrolysate according to certain embodiments of the present disclosure.

FIG. 8 depicts a scheme of an industrial production setup for executing extraction in a single stage mode using liquid-liquid separation centrifuges. Hydrolysate may be fed from feed tank 810 through stream 811 to liquid-liquid separation centrifuges 801 and 802, where it is contacted with organic stream 816 (i.e., the LAEM). After separation, organic stream 812 may be mixed with wash water in a static mixer 831, and separated in a decanter centrifuge 832. Aqueous streams 813, from centrifuges 801 and 802, may be combined with the aqueous stream 814 from the decanter centrifuge to form the sugar stream which is sent for further polishing and concentrating. Organic stream 815 may be sent to a neutralizing tank 840, where it is mixed with an aqueous slurry or solution of base. The resulting solution can be sent through stream 841 to liquid-liquid separation centrifuge 803. The aqueous stream coming out of centrifuge 803 can comprise the removed acids and impurities, and may be sent to the waste treatment part of the plant. Organic stream 816 may comprise the recycled LAEM. The recycled LAEM may be sent back to centrifuges 801 and 802 for further extractions. Optionally, about 5%, 10%, 15%, 20% 25% of stream 816 is diverted to stream 817 and tank 820 for LAEM cleaning by contacting the organic stream with an aqueous base solution. The mixture of organic and aqueous phases may be diverted by stream 821 back to mixing tank 840, together with stream 815.

Figure 9:
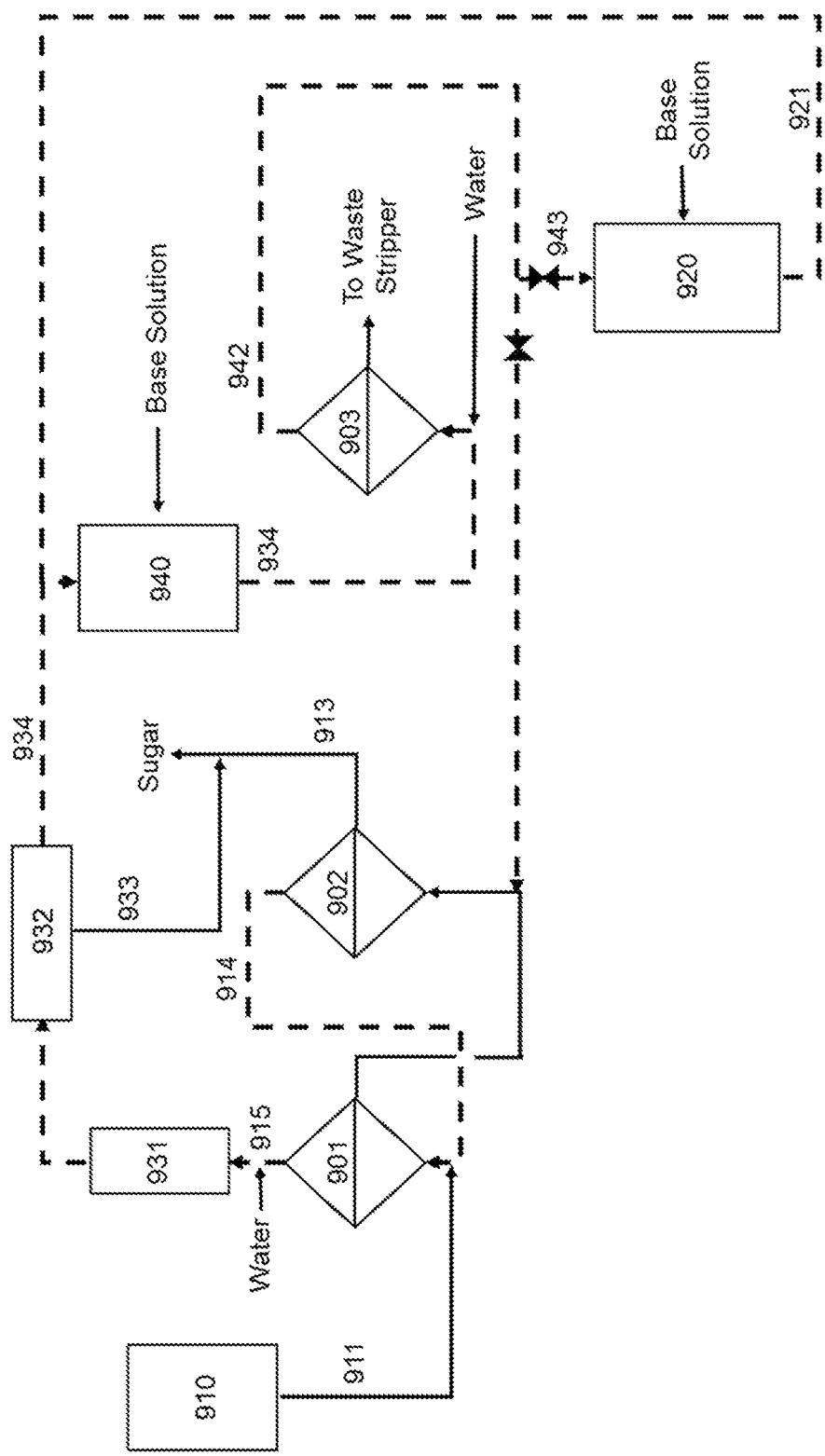
FIG. 9 depicts a scheme of an industrial production setup for refining a lignocellulosic hydrolysate according to certain embodiments of the present disclosure.

FIG. 9 depicts a scheme of industrial production setup for executing extraction in a countercurrent mode using liquid-liquid separation centrifuges. Hydrolysate may be fed from feed tank 910 through stream 911 to liquid-liquid separation centrifuges 901. Aqueous outflow stream 912 can be fed into the liquid-liquid separation centrifuge 902. In a countercurrent mode, centrifuge 2 may also be fed with recycled LAEM stream 942. The organic outflow stream 914 may be fed into centrifuge 901. Loaded LAEM stream 915 can be fed into a static mixer 931. Together with wash water, the mixture can then be separated in a decanter centrifuge 932. The sugar comprising stream 933 can be mixed with a sugar comprising stream 913, and they may be sent for further polishing of the product and concentrating. Organic stream 934, comprising the loaded LAEM, can be mixed with a base solution or suspension in the neutralizing tank 940. The mixture can be fed with 941 into the liquid-liquid separation centrifuge 3. The aqueous outflow stream can be sent to the waste treatment part of the plant. The regenerated LAEM stream 942 may be recycled back for further extraction. At least about 5%, 10%, 15%, 20%, or at least about 25% of stream 932 can be diverted to stream 943 and tank 920 for LAEM cleaning by contacting with an aqueous base solution. Optionally, the mixture of the organic and aqueous phase is diverted by stream 921 back to the mixing tank 940, together with stream 934. In certain aspects of the present disclosure, the aqueous solution or suspension fed into neutralizing tank 920 or 940 may comprise an alkaline metal oxide, alkaline metal hydroxide, alkaline earth metal oxide or alkaline earth metal hydroxide, or mixtures thereof. The aqueous solution may comprise a suspension of lime or NaOH, or a mixture thereof. Optionally, the base is added as an aqueous solution. The neutralization is controlled at a pH between 6 and 8. The pH of neutralizing may be controlled at a pH of at least about 6.0, at least about 6.1, at least about 6.2, at least about 6.3, at least about 6.4, at least about 6.5, at least about 6.6, at least about 6.7, at least about 6.8, at least about 6.9, at least about 7.0, at least about 7.1, at least about 7.2, at least about 7.3, at least about 7.4, at least about 7.5, at least about 7.6, at least about 7.7, at least about 7.8, at least about 7.9, or at least about 8.0. Optionally, the aqueous solution or suspension fed into the solvent cleaning tank 920 comprises an alkaline metal oxide, alkaline metal hydroxide, alkaline earth metal oxide or alkaline earth metal hydroxide, or mixtures thereof. The aqueous solution may be a suspension comprising lime or NaOH, or a mixture thereof. The pH of solvent cleaning may be controlled at pH of at least about 13.0, at least about 13.5, at least about 14.0, or at least about 14.5. Optionally, the pH of the LAEM cleaning is at least about 13.0, at least about 13.5, at least about 14.0, or at least about 14.5. The excess base equivalents of LAEM cleaning may be utilized for LAEM neutralization.

The LAEM can be recycled by contact with a base to a very high efficiency. For example, during 365 days of continuous operation, only at most about 0.5%, at most about 1%, at most about 1.5%, at most about 2%, at most about 2.5%, at most about 3%, at most about 3.5%, at most about 4%, at most about 4.5%, at most about 5%, or at most about 5.5% of LAEM, such as 2% to 3.5% of LAEM may be lost to waste streams. The lifetime service of the initial charge of the LAEM may be at least about 5 years, at least about 7 years, at least about 9 years, at least about 11 years, at least about 13 years, at least about 15 years, at least about 17 years, or at least about 19 years, such as 5 years to 11 years. The lifetime service of the LAEM may be at least about 5, at least about 10, at least about 15, at least about 20, at least about 25, at least about 30, at least about 35, or at least about 40 times, such as about 15 to 35 times that of a WBA that would have the same capacity for refining lignocellulosic hydrolysates of bagasse. The LAEM may be recycled at least about 20, at least about 25, at least about 30, at least about 35, at least about 40, at least about 45, at least about 50, at least about 55, or at least about 60 times a day, such as 30 to 45 times a day. In some examples, the non-recoverable stream may be at most 1%, at most 5%, at most 10%, at most 15%, or at most 20% of the total solvent stream, such as 5% to 15% of the total solvent stream. In another example, the amount of sweet water generated is at most about 0.5, at most about 0.55, at most about 0.6, at most about 0.65, at most about 0.7, at most about 0.75, or at most about 0.8, such as 0.55 to 0.75 compared to the amount of sweet water generated by a WBA system of the same capacity when refining lignocellulosic hydrolysates of bagasse. The energy required for concentrating the sweet water may be at most about 0.5, at most about 0.55, at most about 0.6, at most about 0.65, at most about 0.7, at most about 0.75, or at most about 0.8, such as 0.55 to 0.7 compared to the amount of energy required to concentrate sweet water generated by a WBA system of the same capacity when refining lignocellulosic hydrolysates of bagasse. In another example, the amount of ash generated as a waste product of regenerating the weak base site of the LAEM may be at most 0.05, at most 0.1, at most 0.15, at most 0.2, at most 0.25, at most 0.30, at most 0.35, or at most 0.4, such as 0.15 to 0.30 compared to the amount of ash generated in the regeneration of a WBA system of the same capacity when refining lignocellulosic hydrolysates of bagasse.

A system described herein may comprise a sensing unit in fluid communication with the refining unit to analyze the refined aqueous stream. The sensing unit may analyze the refined aqueous stream continuously or in batches. In some examples, the sensing unit may comprise a pH probe. Optionally, if the pH probe detects that the pH of the refined aqueous stream is too acidic, such as pH less than about 3.0, the sensing unit may divert the stream away from the fermentation unit. In some examples, if a pH probe may detect that the pH of the refined aqueous stream is too acidic, the sensing unit is configured to raise the pH of the solution, for example, by addition of ammonia. In some examples, the sensing unit may analyze the color of the refined aqueous stream, for example, using a spectrophotometer. If the light absorbance at a particular wavelength is determined to be too high, the sensing unit may divert the stream away from the fermentation unit. In some examples, the sensing unit can analyze conductivity of the refined aqueous stream, for example, using a conductivity probe. If the conductivity is determined to be too high, such as conductivity greater than 10,000 $\mu S/cm$, the sensing unit may divert the stream away from the fermentation unit. In some examples, the sensing unit can analyze the density of the refined aqueous stream, for example, using a refractometer. If the density is determined to be too high or too low, such as a density corresponding to a sugar concentration outside the range of 50 g/L to 300 g/L, the sensing unit may divert the stream away from the fermentation unit, or may cause the addition of water to dilute the stream. The sensing unit may be configured to analyze concentration of one or more components of the refined aqueous stream, wherein the one or more components are selected from xylose, arabinose, hexoses, glucose, galactose, mannose, fructose, disaccharides, oligosaccharides, ash, phenolic compounds, furfural, and hydroxymethylfurfural. Any concentration outside the ranges described for the subject methods and compositions may cause the sensing unit to divert the stream away from the fermentation unit, or to correct the concentration by suitable concentration or dilution. Any stream diverted from the fermentation unit may be further refined or utilized in some other process of the plant.

The acid-depleted hemicellulose sugar stream (i.e., the refined aqueous stream) can be further purified. For example, residual diluent in the acid-depleted hemicellulose sugar stream can be removed using a packed distillation column. The distillation can remove at least 70%, 80%, 90%, or 95% of the diluent, such as 80% to 85% of the diluent, in the acid-depleted hemicellulose sugar stream. With or without a diluent distillation step, the acid-depleted hemicellulose sugar stream can also be contacted with an SAC exchanger to remove any residual metallic cations and any residual amines. Preferably, the acid-depleted hemicellulose sugar stream can be purified using a packed distillation column followed by a SAC exchanger.

Preferably, the acid-depleted hemicellulose sugar stream can then be contacted with a WBA exchanger to remove excess protons. The amine-removed and neutralized hemicellulose sugar stream can be pH adjusted and evaporated to 25-65% and preferably 30-40% weight/weight dissolved sugars in any conventional evaporator, e.g., a multiple effect evaporator or a mechanical vapor recompression (MVR) evaporator.

Any residual solvent present in the hemicellulose sugar stream can also be removed by evaporation. For example, the solvent that forms a heterogeneous azeotrope with water can be separated and returned to the solvent cycle. Optionally, the concentrated sugar solution can be contacted with activated carbon to remove residual organic impurities. The concentrated sugar solution may also be contacted with a mixed bed resin system to remove any residual ions or color bodies. Optionally, the now refined sugar solution can be concentrated further by a conventional evaporator or MVR.

The resulting stream may be a highly purified hemicellulose sugar mixture (e.g., 436 in FIG. 4) comprising, e.g., 85-95% weight/weight monosaccharides out of the total dissolved sugars. The composition of the sugars can depend on the composition of the starting biomass. A hemicellulose sugar mixture produced from softwood biomass can have 65-75% (weight/weight) C6 saccharides in the sugar solution out of total sugars. In contrast, a hemicellulose sugar mixture produced from hardwood biomass can contain 80-85% weight/weight C6 sugars out of total sugars. The purity of the stream in all cases may be sufficient for fermentation processes and/or catalytic processes utilizing these sugars.

The highly purified hemicellulose sugar mixture 436 may be characterized by one or more, two or more, three or more, four or more, five or more, six or more characteristics including (i) monosaccharides in a ratio to total dissolved sugars >0.50 weight/weight; (ii) glucose in a ratio to total monosaccharides <0.25 weight/weight; (iii) xylose in a ratio to total monosaccharides >0.18 weight/weight; (iv) fructose in a ratio to total monosaccharides <0.10 weight/weight; (v) fructose in a ratio to total monosaccharides >0.01 weight/weight; (vi) furfurals in amount up to 0.01% weight/weight; (vii) phenols in amounts up to 500 ppm; and (viii) a trace amount of 2-ethyl-1-hexanol. For example, the sugar mixture can be a mixture having a high monosaccharides to total dissolved sugars ratio, a low glucose content, and a high xylose content. The sugar mixture can be a mixture having a high monosaccharides to total dissolved sugars ratio, a low glucose content, a high xylose content, and a low impurity contents (e.g., low furfurals and phenols). The mixture can be characterized by a high monosaccharides to total dissolved sugars ratio, a low glucose content, a high xylose content, a low impurity contents (e.g., low furfurals and phenols), and a trace amount of 2-ethyl-1-hexanol.

The resulting stream can be a sugar mixture with a high monomeric ratio. In some sugar mixture, the monosaccharides to total dissolved sugars ratio is larger than 0.50, 0.60, 0.70, 0.75, 0.80, 0.85, 0.90, or 0.95 weight/weight, such as 0.75 to 0.90 weight/weight. The aqueous stream (refined hemicellulose sugar stream) may comprise less than 14%, less than 12%, less than 10%, less than 8%, less than 6%, less than 4%, or less than 2% weight/weight of arabinose, such as 6% to 12% of arabinose relative to total dissolved sugars. The refined hemicellulose sugar stream may comprise less than 10%, less than 8%, less than 6%, less than 4%, or less than 2% weight/weight of disaccharides, such as 4% to 8% weight/weight of disaccharides, relative to total dissolved sugars. The resulting stream may be a sugar mixture having a low glucose content. In some sugar mixture, the glucose to total monosaccharides ratio is less than 0.25, 0.20, 0.15, 0.13, 0.10, 0.06, 0.05, 0.03, or 0.02 weight/weight, such as 0.05 to 0.15 weight/weight glucose. Optionally, the resulting stream is a sugar mixture with a high xylose content. In some sugar mixture, the xylose to total monosaccharides ratio may be larger than 0.10, 0.15, 0.18, 0.20, 0.30, 0.40, 0.50, 0.60, 0.70, 0.80 or 0.85 weight/weight, such as 0.20 to 0.50 weight/weight xylose.

In some sugar mixtures 436, the fructose to total dissolved sugars ratio can be less than 0.02, 0.03, 0.04, 0.05, 0.06, 0.07, 0.08, 0.09, 0.10, 0.15, 0.20, 0.25 or 0.30 weight/weight, such as 0.07 to 0.20 weight/weight. In some sugar mixtures 436, the fructose to total dissolved sugars ratio may be larger than 0.001, 0.002, 0.005, 0.006, 0.007, 0.008, 0.009, 0.01, 0.02, 0.03, 0.04, 0.05, 0.06, 0.07, 0.08, or 0.09 weight/weight, such as 0.01 to 0.05 weight/weight.

The above hemicellulose sugar mixture can include a very low concentration of impurities (e.g., furfurals and phenols). In some resulting streams, the sugar mixture may have furfurals in an amount up to 0.1%, 0.05%, 0.04%, 0.03%, 0.04%, 0.01%, 0.075%, 0.005%, 0.004%, 0.002%, or 0.001% weight/weight, such as 0.01% to 0.04% weight/weight. In some resulting streams, the sugar mixture may have phenolic compounds in an amount up to 700 ppm, 600 ppm, 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm, such as 30 ppm to 100 ppm. The hemicellulose sugar mixture can be further characterized by a trace amount of 2-ethyl-1-hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, or less than 0.001% weight/weight 2-ethyl-1-hexanol.

This high purity sugar solution can be used to produce industrial products and consumer products as described in PCT/IL2011/00509 (incorporated herein by reference for all purposes). Furthermore, the softwood sugar product containing 65-75% weight/weight C6 sugars can be used as fermentation feed to species that are only able to utilize C6 sugars, and the resulting mix of C5 and product may be separated, the C5 can then be refined to obtain a C5 product, as described in PCT/US2011/50435 (incorporated herein by reference for all purposes).

A fermentation product can include at least one member selected from the group consisting of alcohols, carboxylic acids, amino acids, monomers for the polymer industry and proteins and wherein the method further comprises processing said fermentation product to produce a product selected from the group consisting of detergent, polyethylene-based products, polypropylene-based products, polyolefin-based products, polylactic acid (polylactide)-based products, polyhydroxyalkanoate-based products and polyacrylic-based products. These fermentation products may be used alone or with other components as food or feed, pharmaceuticals, nutraceuticals, plastic parts or components to make various consumer products, fuel, gasoline, chemical additive or surfactant.

The high purity sugar solution products may be suitable for chemical catalytic conversions since catalysts are usually sensitive to impurities associated with biomass and sugar degradation products. Typically, the purity may be greater than 95, 96, 97, 98%, preferably greater than 99, 99.5, or 99.9%. This product may comprise small amounts of marker molecules including, for example, residual diluent, e.g., hexanol, 2-ethyl-1-hexanol, kerosene or any other diluents used, as well as furfural, hydroxymethylfurfural, products of furfural or hydroxymethylfurfural condensation, color compounds derived from sugar caramelization, levulinic acid, acetic acid, methanol, galacturonic acid or glycerol.

Once hemicellulose sugars are extracted, the lignocellulosic remainder stream can be subjected to cellulose hydrolysis to obtain an acidic cellulosic hydrolysate stream and acidic lignin stream. The acidic cellulosic hydrolysate stream can be refined using an LAEM as described herein to produce an aqueous stream comprising one or more cellulose sugars.

EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be included within the spirit and purview of this application and scope of the appended claims.

Example 1—Extraction and Refining of Bagasse

Bagasse sugar composition (DB4D01): Bagasse was shredded in a wood shredder. In a temperature controlled tank, bagasse (60 lbs, dry base) was then treated with an aqueous solution containing 0.5% $H_2SO_4$ (wt/wt) at a liquid to solid ratio of 14:2. The average temperature of the temperature controlled tank was maintained at 130-135° C. for 3 hours. The solution was circulated by pumping. The resulting liquor was collected and the solids washed with water. The wash water was then used to prepare the acid solution for the next batch by adding acids as needed. The hemicellulose-depleted lignocellulosic matter was collected and dried.

The acidic hemicellulose sugar stream was run through a SAC column. The sugar stream was then extracted continuously in a series of liquid-liquid separation centrifuges (2 countercurrent stages) with an LAEM having tri-laurylamine: 2-ethyl-1-hexanol at a ratio of 30:70. The LAEM to sugar stream ratio was kept in the range of 2:1 to 1.5:1. The resulting aqueous phase was further purified using a SAC resin, a WBA resin, and a mixed bed resin. The pH of the resulting stream was adjusted to 4.5 with 0.5% HCl, and the sugar solution evaporated to a concentration of ~30% dissolved solids (DS). The resulting sugar stream contained about 7% arabinose, 2.5% galactose, 6.5% glucose, 65% xylose, 1.5% mannose, 4% fructose and 14% oligosaccharides (all % weight/total sugars). This sugar solution was further processed by fractionation on an SSMB system, resulting in a xylose rich fraction and a xylose depleted fraction. Each fraction was concentrated by evaporation. Table 1 provides a chemical analysis of the resulting xylose rich sugar solution.

TABLE 1

Chemical analysis of a hemicellulose sugar mixture produced by hemicellulose sugar extraction and purification of bagasse

| PARAMETER | RESULT | UNITS |
|---|---|---|
| Appearance | Colorless | |
| pH | 3.58 | |
| Saccharides | | |
| % TS (HPLC) | 68.2 | % w/w |
| Composition (HPAE-PAD) | | |
| XYLOSE | 81.84 (55.81) | %/TS (% w/w) |
| ARABINOSE | 4.38 (2.99) | %/TS (% w/w) |
| MANNOSE | 1.99 (1.36) | %/TS (% w/w) |
| GLUCOSE | 5.07 (3.46) | %/TS (% w/w) |
| GALACTOSE | 0.91 (0.62) | %/TS (% w/w) |
| FRUCTOSE | 6.15 (4.20) | %/TS (% w/w) |
| Impurities | | |
| Furfurals (GC) | <0.005 | % w/w |
| Phenols (FC) | 0.04 | % w/w |
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | <2 | ppm |
| S | <10 | ppm |
| P | <10 | ppm |

Example 2—Extraction of Lignocellulosic Hydrolysate with 2-Ethyl-1-Hexanol

The careful design of the industrial plant to achieve high throughput of the refining sequence may be vital in order to achieve reasonable production rate and economics. A liquid-liquid separation centrifuge such as the Rousselet Robatel model BXP 190, nominal capacity 15 gpm can be used. The Rotabel is a pilot scale centrifuge and can be scalable to industrial size.

The sugar stream was extracted continuously in a series of liquid-liquid separation centrifuges (2 countercurrent stages) with an LAEM having tri-laurylamine: 2-ethyl-1-hexanol at a ratio of 30:70. During extraction, contaminants diffuse across the interface of the organic and aqueous phases. Strong mixing can result in a large surface contact area. After diffusion has occurred, fast phase separation can result in high throughput of the system. To achieve this, careful selection of the diluent and optimal mechanical means for mixing and separation may be necessary.

Extraction relies on the diffusion of contaminants across the interface of the two phases. As a result, it is preferable to create a large surface by strong mixing. However, once diffusion occurs it is desired to have fast phase separation to allow high throughput in the system. These requirements can be optimized by selection of the organic phase and by optimizing the mechanical means used for mixing and for separation.

Single contact data in Table 2 shows that 2E1H, which is more hydrophobic, is less effective than hexanol at extracting impurities. This has been studied on a series of typical impurities that can be found in the hydrolysate. Table 2 shows that similar amounts of mineral acid were removed by organic phases comprising either hexanol or 2-ethyl-1-hexanol. However, the ability of 2E1H to remove organic acids and furfural from the hydrolysate was limited. The total acidity was measured by titration of the aqueous phase, while the specific acid species were quantified by HPLC. Sulfuric acid contributed the majority of the total acidity.

TABLE 2

Comparison of impurity removal using hexanol and 2-ethyl-1-hexanol

| Parameter | 70:30 hexanol:TLA | 70:30 2E1H:TLA |
|---|---|---|
| Total acid removal | 94.3% | 94.8% |
| Acetic acid removal | 91.7% | 71.8% |
| Formic acid removal | 91.1% | 72.0% |
| Levulinic acid removal | 91.0% | 59.3% |
| Furfural removal | 79.7% | 76.0% |

Figure 10:
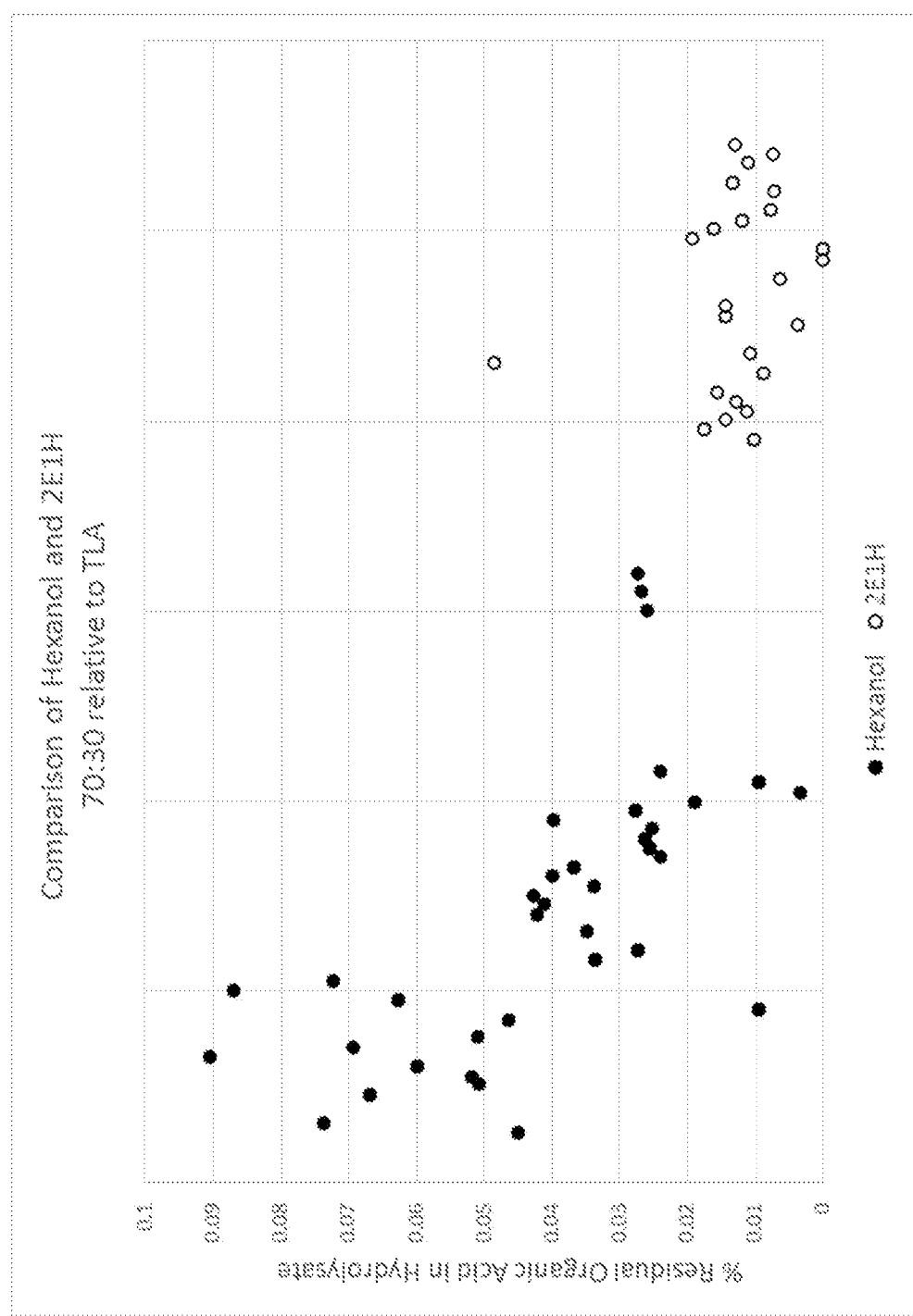
FIG. 10 depicts a comparison of the amount of residual organic acid in a refined hydrolysate when the diluent is either hexanol or 2-ethyl-1-hexanol.

When conducting the process using the Robatel centrifuge, the relative hydrophobicity of hexanol resulted in a slow separation of the mixed solvents and slow operation of the system. Surprisingly, 2-ethyl-1-hexanol was found to be a more preferred diluent in a continuous process using a liquid-liquid separation centrifuge, such as the Robatel centrifuge described herein. As shown in FIG. 10, 2-ethyl-1-hexanol removes organic acids from the hydrolysate more efficiently than hexanol in the continuous process. Not wishing to be bound by any particular theory, the greater hydrophobicity of 2-ethyl-1-hexanol is believed to contribute to the improved performance in the continuous process. As a result, less solvent is entrained in the aqueous phase, resulting in better and more consistent performance. On an industrial scale, the continuous LAEM extraction process with 2E1H results in fast separation of the organic and aqueous phases using less energy than would be required for acid-removal processes typically used in the sugar refining industry.

It should be understood from the foregoing that, while particular implementations have been illustrated and described, various modifications may be made thereto and are contemplated herein. An embodiment of one aspect of the disclosure may be combined with or modified by an embodiment of another aspect of the disclosure. It is not intended that the invention(s) be limited by the specific examples provided within the specification. While the invention(s) has (or have) been described with reference to the aforementioned specification, the descriptions and illustrations of embodiments of the invention(s) herein are not meant to be construed in a limiting sense. Furthermore, it shall be understood that all aspects of the invention(s) are not limited to the specific depictions, configurations or relative proportions set forth herein which depend upon a variety of conditions and variables. Various modifications in form and detail of the embodiments of the invention(s) will be apparent to a person skilled in the art. It is therefore contemplated that the invention(s) shall also cover any such modifications, variations and equivalents.

What is claimed is:

1. A method for refining a lignocellulosic hydrolysate, the method comprising:
   (a) contacting the lignocellulosic hydrolysate with a liquid anion exchange medium (LAEM) in a separation system comprising two liquid-liquid separation centrifuges fluidically coupled in counter-current mode to form a mixture;
   (b) separating the mixture in the separation system into an organic stream and an aqueous stream, wherein the organic stream comprises the LAEM, a mineral acid and an impurity selected from the group consisting of an organic acid, a lignin, a phenol, and a furfural, and wherein the aqueous stream comprises one or more sugars;
   (c) contacting the organic stream with a base, thereby forming a neutralized mixture; and
   (d) recovering a portion of the LAEM from the neutralized mixture;
   wherein steps (a) through (b) are a continuous process.

2. The method of claim 1, wherein steps (a) through (d) are a continuous process.

3. The method of claim 1, wherein steps (a) through (d) are completed within 90 min.

4. The method of claim 1, further comprising washing the organic stream with water to remove residual sugar from the organic stream, thereby forming a dilute sugar water solution and a washed organic stream.

5. The method of claim 4, wherein the dilute sugar water solution is combined with the aqueous stream, wherein the combined stream comprises at least 3.8% wt/wt sugars.

6. The method of claim 1, wherein the base is added as an aqueous suspension or solution.

7. The method of claim 1, wherein the base is lime or NaOH.

8. The method of claim 1, wherein a pH of the neutralized mixture is between 6 and 7.

9. The method of claim 1, further comprising washing the portion of the LAEM with water, thereby forming a washed LAEM.

10. The method claim 9, further comprising contacting a portion of the washed LAEM with a second base.

11. The method of claim 1, wherein the portion of the washed LAEM comprises less than 20% of the washed LAEM, and wherein a pH of the base is at least 13.

12. The method of claim 1, further comprising repeating steps (a)-(d), wherein the portion of the LAEM recovered in step (d) is reused in step (a) as a portion of the LAEM when repeating the steps (a)-(d).

13. The method of claim 12, wherein a volume of the portion of the LAEM after the repeating is at least 80% of the volume of the LAEM before the repeating.

14. The method of claim 13, wherein the repeating occurs at least 45 times in a day.

15. The method of claim 1, wherein a ratio of the LAEM to the lignocellulosic hydrolysate is less than 5:1.

16. The method of claim 1, wherein the LAEM comprises an amine, wherein the amine comprises at least 20 carbon atoms.

17. The method of claim 16, wherein the LAEM further comprises a diluent, wherein the diluent comprises a $C_{6-16}$ alcohol or kerosene.

18. The method of claim 17, wherein a ratio of the amine to the diluent is between 1:7 and 7:1 weight/weight.

19. The method of claim 1, wherein the lignocellulosic hydrolysate comprises at least 0.1% acid weight/weight.

20. The method of claim 19, wherein the lignocellulosic hydrolysate comprises the mineral acid and an organic acid.

21. The method of claim 1, wherein the one or more sugars in the aqueous stream comprises arabinose in an amount up to 12% weight/weight relative to total dissolved sugars.

22. The method of claim 1, wherein the one or more sugars in the aqueous stream comprises disaccharides in an amount up to 8% weight/weight relative to total dissolved sugars.

23. The method of claim 1, wherein the aqueous stream comprises ash in an amount up to 0.25% weight/weight.

24. The method of claim 1, wherein the aqueous stream comprises less than 1000 ppm of an acid selected from the group consisting of acetic acid, formic acid, sulfuric acid, and hydrochloric acid.

25. The method of claim 1, wherein the aqueous stream comprises less than 0.5% weight/weight of the mineral acid.

\* \* \* \* \*

UNITED STATES PATENT AND TRADEMARK OFFICE
CERTIFICATE OF CORRECTION

PATENT NO. : 10,767,237 B2
APPLICATION NO. : 16/311364
DATED : September 8, 2020
INVENTOR(S) : Robert Jansen et al.

It is certified that error appears in the above-identified patent and that said Letters Patent is hereby corrected as shown below:

In the Claims (Claim 11) Column 34, Line 32, replace "claim 1" with -- claim 10 --

(Claim 20) Column 34, Line 57, replace "an organic acid." with -- the organic acid. --

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*